(12) United States Patent
Mayser et al.

(10) Patent No.: US 12,274,775 B2
(45) Date of Patent: *Apr. 15, 2025

(54) **FATTY ACID ESTERS AS ANTI-*MALASSEZIA* AGENTS**

(71) Applicant: SYMRISE AG

(72) Inventors: Peter Mayser, Biebertal (DE); Manuel Pesaro, Holzminden (DE); Gerhard Schmaus, Höxter (DE); Jessica Grieger, Höxter (DE); Nikolas Bugdahn, Holzminden (DE)

(73) Assignee: SYMRISE AG, Holzminden (DE)

( * ) Notice: Subject to any disclaimer, the term of this patent is extended or adjusted under 35 U.S.C. 154(b) by 418 days.

This patent is subject to a terminal disclaimer.

(21) Appl. No.: 17/428,309

(22) PCT Filed: Feb. 4, 2019

(86) PCT No.: PCT/EP2019/052576
§ 371 (c)(1),
(2) Date: Aug. 4, 2021

(87) PCT Pub. No.: WO2020/160741
PCT Pub. Date: Aug. 13, 2020

(65) Prior Publication Data
US 2022/0142885 A1    May 12, 2022

(51) Int. Cl.
| | | |
|---|---|---|
| *A61K 8/37* | (2006.01) | |
| *A61K 8/34* | (2006.01) | |
| *A61Q 5/00* | (2006.01) | |
| *A61Q 17/00* | (2006.01) | |
| *A61Q 19/00* | (2006.01) | |

(52) U.S. Cl.
CPC .............. *A61K 8/375* (2013.01); *A61K 8/345* (2013.01); *A61Q 5/006* (2013.01); *A61Q 17/005* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 2010/0034761 A1* | 2/2010 | Fenyvesi | ............... | A61Q 17/04 424/59 |
| 2010/0215775 A1* | 8/2010 | Schmaus | ............... | A61K 9/0014 514/588 |
| 2014/0328953 A1 | 11/2014 | Kwack et al. | | |

FOREIGN PATENT DOCUMENTS

| | | |
|---|---|---|
| DE | 3314786 A1 | 10/1984 |
| DE | 102013009616 A1 | 12/2014 |
| EP | 1864657 A1 | 12/2007 |
| EP | 1923041 A1 | 5/2008 |
| JP | H09110648 A | 4/1997 |
| JP | 2002114669 A | 4/2002 |
| KR | 20170136478 A | 12/2017 |
| SU | 1286204 A1 | 1/1987 |
| WO | 2011101239 A2 | 8/2011 |
| WO | 2018012021 A1 | 1/2018 |
| WO | 2018224413 A1 | 12/2018 |

OTHER PUBLICATIONS

International Search Report and Written Opinion issued on Oct. 16, 2019 for corresponding PCT Application No. PCT/EP2019/052576.
Indonesian Office Action issued on Apr. 30, 2024 for corresponding ID Application No. P00202106950.
Brazilian Office Action issued on Apr. 22, 2024 for corresponding BR Application No. BR 11 2021 015252-0.
Colombian Office Action issued on Sep. 23, 2024 for corresponding Colombian Application No. NC2021/0011652.
Chinese Office Action issued Jun. 14, 2024 for corresponding Chinese Application No. 201980093959.5.

* cited by examiner

*Primary Examiner* — Jennifer A Berrios
(74) *Attorney, Agent, or Firm* — POLSINELLI PC

(57) ABSTRACT

The present invention primarily relates to a fatty acid ester or mixture of two or more fatty acid esters or mixture comprising one or more fatty acid esters, wherein the fatty acid ester or one, two, three or more, preferably all, of the fatty acid ester(s) is/are selected from the group consisting of 3-hydroxypropyl caprylate, glyceryl monocaprylate, 3-hydroxypropyl undecylenate and glyceryl monoundecylenate, for use in the treatment of an excess of *Malassezia* on the skin surface of mammals, preferably of humans. The present invention further relates to particular mixtures or products, and to the cosmetic, non-therapeutic use of fatty acid esters or of mixtures or products comprising fatty acid esters as defined herein to reduce the amount of *Malassezia* on the skin surface of mammals, preferably of humans.

20 Claims, 5 Drawing Sheets

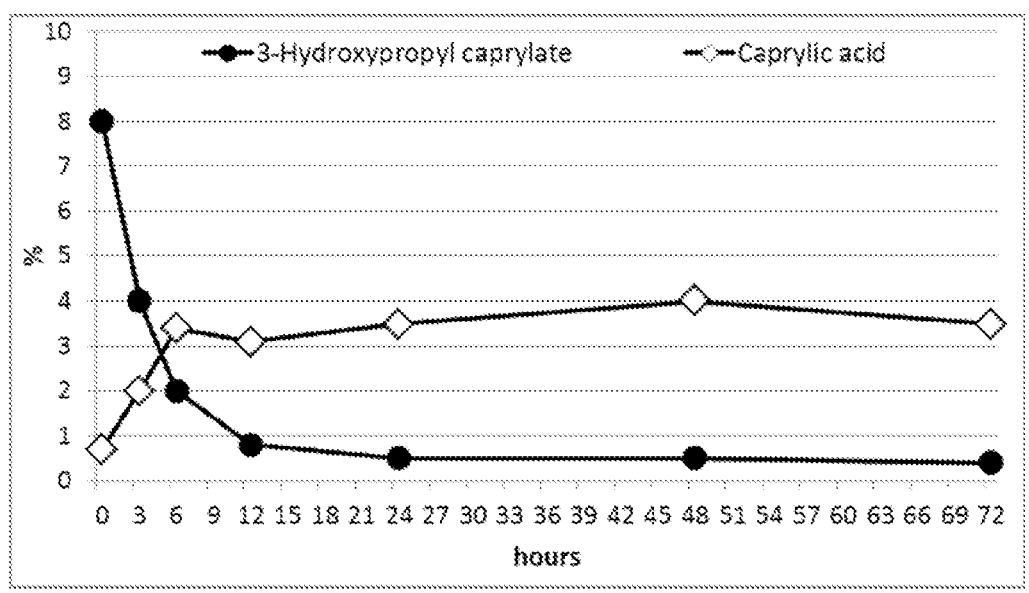
FIG. 1: Cleavage of 3-hydroxypropyl caprylate by *M. globosa* CBS 7705 and subsequent liberation of the active principle caprylic acid. Amounts for each of the chemical species are indicated as percent by weight (y-axis).

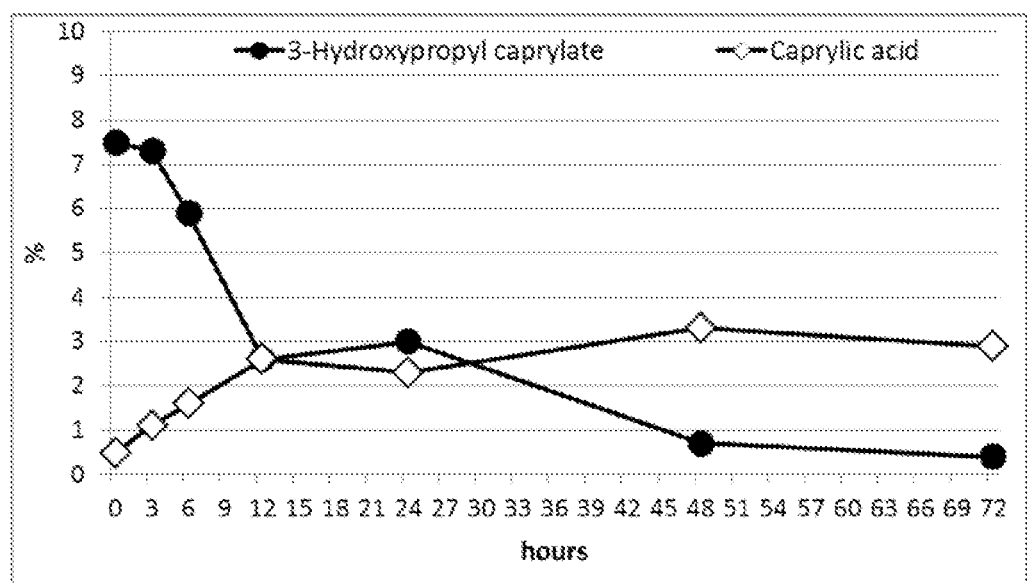
FIG. 2: Cleavage of 3-hydroxypropyl caprylate by *M. restricta* CBS 7877and subsequent liberation of the active principle caprylic acid. Amounts for each of the chemical species are indicated as percent by weight (y-axis).

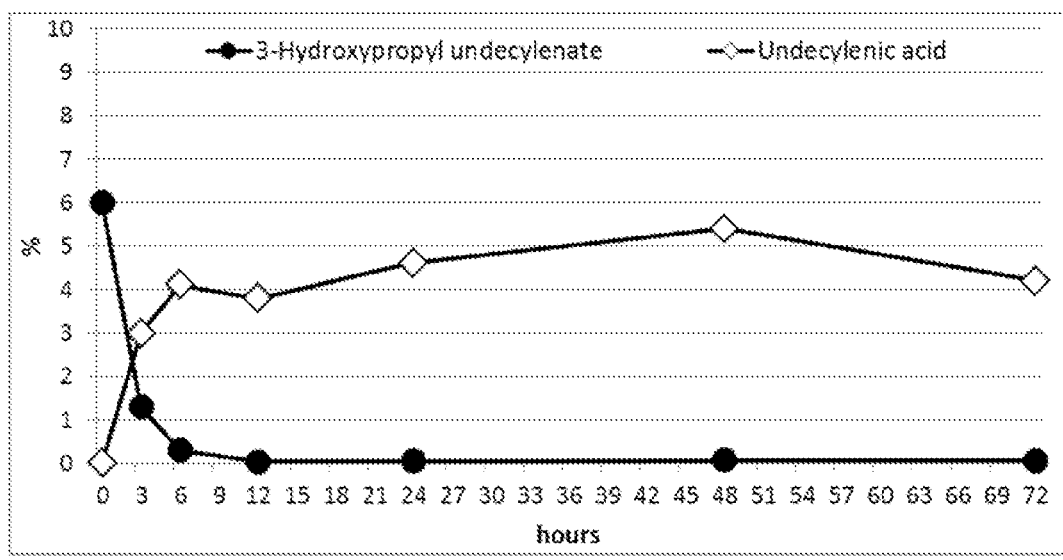
FIG. 3: Cleavage of 3-hydroxypropyl undecylenate by *M. globosa* CBS 7705 and subsequent liberation of the active principle undecylenic acid. Amounts for each of the chemical species are indicated as percent by weight (y-axis).

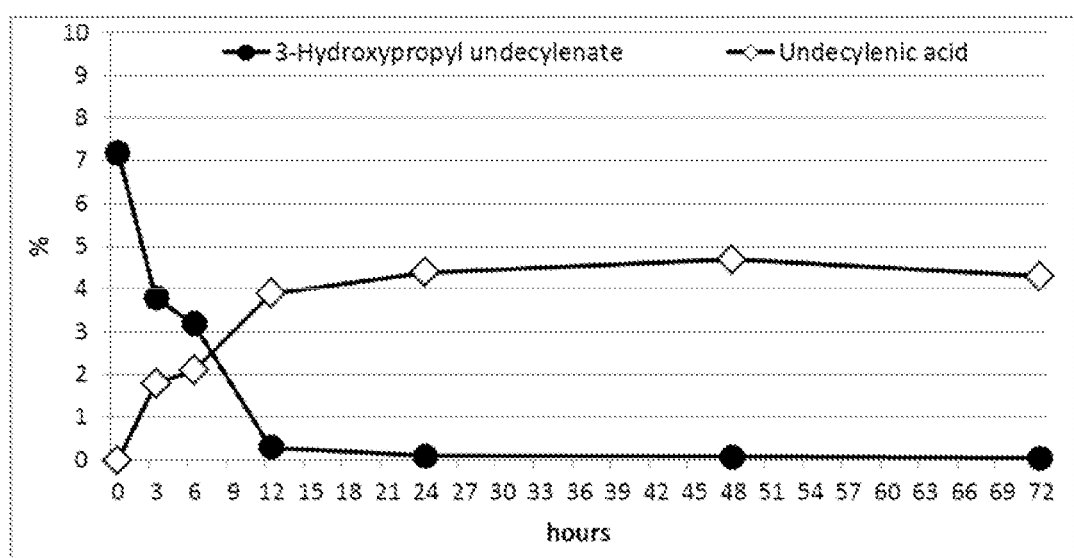
FIG. 4: Cleavage of 3-hydroxypropyl undecylenate by *M. restricta* CBS 7877 and subsequent liberation of the active principle undecylenic acid. Amounts for each of the chemical species are indicated as percent by weight (y-axis).

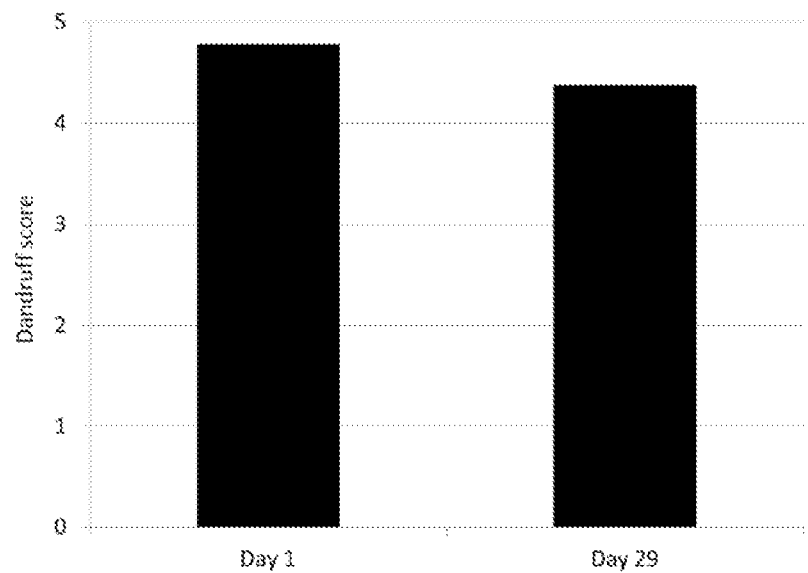
FIG. 5: Significant reduction (p = 0.004) of average dandruff score according to Piérard-Franchimont from marked (4.78) to moderate (4.38) in an in vivo study with 22 participants after 4 weeks of application.

FATTY ACID ESTERS AS ANTI-*MALASSEZIA* AGENTS

CROSS-REFERENCE TO RELATED APPLICATIONS

This application is a national stage application (under 35 U.S.C. § 371) of PCT/EP2019/052576, filed Feb. 4, 2019, which is incorporated herein by reference in its entirety.

The present invention primarily relates to fatty acid esters or mixtures or products comprising fatty acid esters as defined herein for use in the treatment of an excess of *Malassezia* on the skin surface of mammals, preferably of humans. The present invention further relates to particular mixtures or products, and to the cosmetic, non-therapeutic use of fatty acid esters or of mixtures or products comprising fatty acid esters as defined herein to reduce the amount of *Malassezia* on the skin surface of mammals, preferably of humans.

Further aspects of the present invention will arise from the description below, in particular from the examples, as well as from the attached patent claims.

*Malassezia* is a genus of fungi and is naturally found on the skin surfaces of many animals, including humans. It is involved in the pathogenesis of a variety of diseases, in particular skin diseases, and undesired conditions such as, for example, in *Pityriasis versicolor* (tinea *versicolor*), seborrheic dermatitis and dandruff.

Short-chain and medium-chain fatty acids display good antimicrobial activity against *Malassezia*. However, their practical use in topical therapy is limited by their (i) intense smell, (ii) skin irritation, (iii) lack of skin-substantiveness and (iv) the difficulties they pose during formulation into products.

Various esters of said fatty acids do not display these disadvantageous properties. It is known that *Malassezia* is able to cleave such esters and to release the fatty acids, which leads to a "self-kill" of the fungi. However, the hydrolysis rates of esters through *Malassezia* enzymes vary strongly depending on the alcohol component of the esters.

In DE 42 37 367 A1 fatty acid esters are described as antimycotic agents. These esters are preferably selected from the group of hexyl laurate, isopropyl stearate, glyceryl monolaurate, caprylic acid triglyceride and capric acid triglyceride. 1,3-Propanediol esters and glyceryl monoesters are not disclosed.

DE 42 34 188 A1 relates to ethoxylated and propoxylated organic compounds as antimycotic agents in cosmetics.

DE 10 2004 046 603 A1 describes substance mixtures comprising fatty acid esters of polyols and salts of short chain fatty acids to counteract microorganisms. It does not disclose any 1,3-propanediol esters and glyceryl monoesters.

SU 1286204 A1 discloses the use of a mixture of mono- (50-60%), di- (30-35%) and triesters (10-15%) of glycerol and undecylenic acid to give antimicrobial properties to a cosmetic base. 1,3-Propanediol esters as well as activity against *Malassezia* are not described.

DE 33 14 786 A1 discloses a mixture with antimycotic activity comprising mono and/or di-10-undecylenic acid glyceryl esters. The mixtures are used in the treatment of nasal cavity mycosis and onychomycosis. Their use for reducing the amount of *Malassezia* on the skin surface, preferably on the scalp, of mammals is not disclosed.

In WO 2006/054110 A2, esters of 1,2,3-propanetriol with one or more C11 to C24 fatty acids are described, wherein at least one fatty acid has at least one double bond. The application field for these substances is the treatment of chronic inflammatory disorders.

WO 2007/095262 A2 discloses 1,3-propanediol esters for the purpose of dissolving botanical extracts, fragrance concentrates and oils. Antimicrobial effects or benefits for skin and scalp of the 1,3-propanediol esters are not described.

It was thus an object of the present invention to provide more effective and compatible active agents for the treatment of *Malassezia*-associated diseases and undesired conditions, preferably of dandruff on human scalp.

According to a first aspect of the present invention, the stated object is achieved by a fatty acid ester or mixture of two or more fatty acid esters or mixture comprising one or more fatty acid esters, wherein the fatty acid ester or one, two, three or more, preferably all, of the fatty acid ester(s) is/are selected from the group consisting of 3-hydroxypropyl caprylate, glyceryl monocaprylate, 3-hydroxypropyl undecylenate and glyceryl monoundecylenate, preferably wherein the fatty acid ester or one, two or three, preferably all, of the fatty acid ester(s) is/are selected from the group consisting of 3-hydroxypropyl caprylate, glyceryl monocaprylate and 3-hydroxypropyl undecylenate, more preferably wherein the fatty acid ester or one or two, preferably all, of the fatty acid ester(s) is/are selected from the group consisting of 3-hydroxypropyl caprylate and 3-hydroxypropyl undecylenate, for use in the treatment of an excess of *Malassezia* on the skin surface, preferably on the scalp, of mammals, preferably of humans.

Within the framework of the present text, the term "*Malassezia*" refers to one or more species of the genus *Malassezia*, preferably to one, two, three, four, five or more species of the genus *Malassezia* (as defined further below).

*Malassezia* species are naturally found on the skin surfaces of many animals, including humans. As these fungi require fatty acids to grow, they are most common in areas with many sebaceous glands, i.e. on the scalp, face, and upper part of the body. However, when the fungus grows too rapidly, the natural renewal of cells is disturbed and, for example, dandruff appears on the scalp along with an itching sensation.

Within the framework of the present text, an excess of *Malassezia* on the skin surface, preferably on the scalp, of mammals, preferably of humans, thus relates to a situation where the total amount of *Malassezia* cells present on said skin surface leads to symptoms of skin disease such as, for example, redness, itching, dryness, flaking, greasiness, hypopigmentation and/or hyperpigmentation of the skin. The treatment of an excess of *Malassezia* on the skin surface preferably relates to an action that leads to a situation where the total amount of *Malassezia* cells present on said skin surface does not result in said symptoms of skin disease or wherein one, more or preferably all said symptoms are at least reduced.

Thus, preferably a use according to the present invention (as described herein) is selected from or comprises the treatment and/or the prevention of one, more or all symptoms from the group consisting of redness, itching, dryness, flaking, greasiness, hypopigmentation and hyperpigmentation of the skin.

Within the framework of the present text, the term "on the skin surface" also includes the areas of the hair infundibulum, the junctional zone and/or the sebaceous glands, if applicable, where an excess of *Malassezia* may be present.

Caprylate refers to an ester of caprylic acid (CAS Registry Number of caprylic acid: 124-07-2; also known as octanoic acid) and undecylenate refers to an ester of 10-undecylenic acid (CAS Registry Number of 10-undecylenic acid: 112-

38-9; also known as 10-undecenoic acid). 3-Hydroxypropyl caprylate refers to the monoester of the alcohol 1,3-propanediol (CAS Registry Number: 504-63-2) with caprylic acid and 3-hydroxypropyl undecylenate refers to the monoester of the alcohol 1,3-propanediol with 10-undecylenic acid. Glyceryl monocaprylate refers to a monoester of (mono) glycerol (CAS Registry Number: 56-81-5; also known as 1,2,3-propanetriol) with caprylic acid and glyceryl monoundecylenate refers to a monoester of (mono)glycerol with undecylenic acid.

The investigations underlying the present invention surprisingly proved the rapid enzymatic release of caprylic acid and undecylenic acid from the fatty acid esters as defined herein by *Malassezia* strains involved in various undesired skin conditions, such as dandruff. It was particularly surprising to the expert in the field that *Malassezia* strains readily accept the fatty acid esters as defined herein as substrates, since the fatty acids caprylic acid and undecylenic acid are not found in sebum of the human skin. Moreover, since the hydrolysis rates of esters through *Malassezia* enzymes vary strongly depending on the alcohol component of the esters, it was also surprising that the fatty acid esters of 1,3-propanediol and glycerol were effectively hydrolysed by *Malassezia*.

A preferred embodiment of the invention relates to 3-hydroxypropyl caprylate or glyceryl monocaprylate or 3-hydroxypropyl undecylenate or glyceryl monoundecylenate or to a mixture comprising 3-hydroxypropyl caprylate or glyceryl monocaprylate or 3-hydroxypropyl undecylenate or glyceryl monoundecylenate (as the only *Malassezia*-active ingredient in the mixture) for use in the treatment of an excess of *Malassezia* on the skin surface, preferably on the scalp, of mammals, preferably of humans.

Another preferred embodiment of the invention relates to a mixture of 3-hydroxypropyl caprylate and 3-hydroxypropyl undecylenate, or of glyceryl monocaprylate and 3-hydroxypropyl undecylenate, or of 3-hydroxypropyl caprylate and glyceryl monoundecylenate, or of glyceryl monocaprylate and glyceryl monoundecylenate, or of 3-hydroxypropyl caprylate and glyceryl monocaprylate, or to a mixture comprising 3-hydroxypropyl caprylate and 3-hydroxypropyl undecylenate, or glyceryl monocaprylate and 3-hydroxypropyl undecylenate, or 3-hydroxypropyl caprylate and glyceryl monoundecylenate, or glyceryl monocaprylate and glyceryl monoundecylenate, or 3-hydroxypropyl caprylate and glyceryl monocaprylate (as the only *Malassezia*-active ingredients in the mixture) for use in the treatment of an excess of *Malassezia* on the skin surface, preferably on the scalp, of mammals, preferably of humans.

Another preferred embodiment of the invention relates to a mixture of 3-hydroxypropyl caprylate, glyceryl monocaprylate and 3-hydroxypropyl undecylenate, or to a mixture comprising 3-hydroxypropyl caprylate, glyceryl monocaprylate and 3-hydroxypropyl undecylenate (as the only *Malassezia*-active ingredients in the mixture) for use in the treatment of an excess of *Malassezia* on the skin surface, preferably on the scalp, of mammals, preferably of humans.

Another preferred embodiment of the invention relates to a mixture of 3-hydroxypropyl caprylate, glyceryl monocaprylate, 3-hydroxypropyl undecylenate and glyceryl monoundecylenate, or to a mixture comprising 3-hydroxypropyl caprylate, glyceryl monocaprylate, 3-hydroxypropyl undecylenate and glyceryl monoundecylenate (as the only *Malassezia*-active ingredients in the mixture) for use in the treatment of an excess of *Malassezia* on the skin surface, preferably on the scalp, of mammals, preferably of humans.

Another preferred embodiment of the invention relates to a fatty acid ester or mixture of two or more fatty acid esters or mixture comprising one or more fatty acid esters, wherein the fatty acid ester or one, two or three, preferably all, of the fatty acid ester(s) is/are selected from the group consisting of 3-hydroxypropyl caprylate, 3-hydroxypropyl undecylenate and glyceryl monoundecylenate for use in the treatment of an excess of *Malassezia* on the skin surface, preferably on the scalp, of mammals, preferably of humans. More preferably, the fatty acid esters and mixtures for use according to the invention (further) are not or do not comprise any diesters of caprylic acid and/or are not or do not comprise any triesters of caprylic acid and/or are not or do not comprise any ethoxylated variants of caprylic acid and/or are not or do not comprise any diesters of undecylenic acid and/or are not or do not comprise any triesters of undecylenic acid and/or are not or do not comprise any ethoxylated variants of undecylenic acid.

Advantageously, the fatty acid esters or mixtures for use as defined herein show particularly high antimicrobial activity against *Malassezia*. Particularly, binary combinations of fatty acid esters of caprylic acid and of fatty acid esters of undecylenic acid (as defined above) and mixtures comprising the same display a synergistic increase in antimicrobial activity against *Malassezia* (as will be demonstrated further below).

Another preferred embodiment of the invention relates to a mixture for use as defined herein, further comprising one or more 1,2-alkane diol(s), preferably one or more 1,2-alkane diol(s) selected from the group consisting of 1,2-pentanediol, 1,2-hexanediol, 1,2-octanediol and 1,2-decanediol, more preferably one 1,2-alkane diol selected from the group consisting of 1,2-pentanediol, 1,2-hexanediol, 1,2-octanediol and 1,2-decanediol.

A preferred alternative embodiment relates to a fatty acid ester as defined herein for use as defined herein, which is used in combination with one or more 1,2-alkane diol(s), preferably one or more 1,2-alkane diol(s) selected from the group consisting of 1,2-pentanediol, 1,2-hexanediol, 1,2-octanediol and 1,2-decanediol, more preferably one 1,2-alkane diol selected from the group consisting of 1,2-pentanediol, 1,2-hexanediol, 1,2-octanediol and 1,2-decanediol.

Surprisingly, it was found that the addition of one or more 1,2-alkane diol(s) as defined herein to one or more caprylic acid ester(s) or undecylenic acid ester(s) as defined herein, leads to a synergistic increase in antimicrobial activity against *Malassezia* (as will be demonstrated further below).

Thus, another preferred embodiment of the invention relates to a mixture comprising 1,2-pentanediol and 3-hydroxypropyl caprylate, or comprising 1,2-pentanediol and 3-hydroxypropyl undecylenate, or comprising 1,2-hexanediol and 3-hydroxypropyl caprylate, or comprising 1,2-hexanediol and 3-hydroxypropyl undecylenate, or comprising 1,2-octanediol and 3-hydroxypropyl caprylate, or comprising 1,2-octanediol and 3-hydroxypropyl undecylenate, or comprising 1,2-decanediol and 3-hydroxypropyl caprylate, or comprising 1,2-decanediol and 3-hydroxypropyl undecylenate, or comprising 1,2-pentanediol and glyceryl monocaprylate, or comprising 1,2-pentanediol and glyceryl monoundecylenate, or comprising 1,2-hexanediol and glyceryl monocaprylate, or comprising 1,2-hexanediol and glyceryl monoundecylenate, or comprising 1,2-octanediol and glyceryl monocaprylate, or comprising 1,2-octanediol and glyceryl monoundecylenate, or comprising 1,2-decanediol and glyceryl monocaprylate, or comprising 1,2-decanediol and glyceryl monoundecylenate, for use in the treatment of an excess of *Malassezia* on the skin surface, preferably on the scalp, of mammals, preferably of humans.

Another preferred embodiment relates to a fatty acid ester or a mixture for use as defined herein, wherein *Malassezia* is/are one or more species selected from the group consisting of *M. furfur, M. pachydermatis, M. sympodialis, M. globosa, M. obtusa, M. restricta, M. slooffiae, M. dermatis, M. japonica, M. nana, M. yamatoensis, M. caprae, M. equina, M. cuniculi, M. brasiliensis, M. psitaci* and *M. arunalokei*, preferably is/are selected from the group consisting of *M. restricta, M. globosa, M. furfur, M. sympodialis* and *M. dermatis*.

Another embodiment of the present invention relates to a mixture for use as defined herein, wherein the mixture comprising one or more fatty acid esters is a product selected from the group consisting of leave-on skin care product, preferably oil in water emulsion or water in oil emulsion, and rinse-off skin care product, preferably shampoo, more preferably anti-dandruff shampoo.

It is advantageous to formulate the mixtures for use as defined herein in a way that enables users to incorporate the treatment of an excess of *Malassezia* on their skin surface into their daily hair or skin care routine. This is achieved by, for example, formulating said mixtures as hair or skin care products. By creating hair or skin care products comprising one or more fatty acid esters for use as defined herein, e.g. an anti-dandruff shampoo, the user can save time, money and effort by combining the treatment against an excess of *Malassezia* on the skin surface with their standard hair or skin care, e.g. washing hair. The rinse-off skin care product as defined herein may also, for example, be a shower gel and the leave-on skin care product may, for example, be a body cream or body lotion.

Another preferred embodiment of the present invention relates to a mixture for use as defined herein, comprising one or more additional active agent(s), preferably one or more antimicrobial agent(s), more preferably one or more active agent(s) selected from the group consisting of clotrimazole (CAS Registry Number 23593-75-1), bifonazole (CAS Registry Number 60628-96-8), miconazole (CAS Registry Number 22916-47-8), ketoconazole (CAS Registry Number 65277-42-1), fluconazole (CAS Registry Number 86386-73-4), climbazole (CAS Registry Number 38083-17-9), itraconazole (CAS Registry Number 84625-61-6), terbinafine (CAS Registry Number 91161-71-6), nystatin (CAS Registry Number 1400-61-9), amorolfine (CAS Registry Number 78613-35-1), ciclopirox (CAS Registry Number 29342-05-0), octopirox (CAS Registry Number 68890-66-4) and undecylenic acid (CAS Registry Number 112-38-9).

A preferred alternative embodiment relates to a fatty acid ester for use as defined herein, which is used in combination with one or more additional active agent(s), preferably with one or more antimicrobial agent(s), more preferably with one or more active agent(s) selected from the group consisting of clotrimazole, bifonazole, miconazole, ketoconazole, fluconazole, climbazole, itraconazole, terbinafine, nystatin, amorolfine, ciclopirox, octopirox and undecylenic acid.

Another aspect of the present invention relates to a mixture, preferably a product selected from the group consisting of leave-on skin care product, preferably oil in water emulsion or water in oil emulsion, and rinse-off skin care product, preferably shampoo, more preferably anti-dandruff shampoo, comprising 3-hydroxypropyl caprylate and 3-hydroxypropyl undecylenate, or comprising glyceryl monocaprylate and 3-hydroxypropyl undecylenate, or comprising 3-hydroxypropyl caprylate and glyceryl monoundecylenate, or comprising glyceryl monocaprylate and glyceryl monoundecylenate, or comprising 3-hydroxypropyl caprylate and glyceryl monocaprylate.

According to a preferred embodiment, the total amount of the fatty acid ester(s) (as defined herein) comprised in the mixture or product as defined herein is from 0.02 to 5 wt.-%, more preferably from 0.05 to 2 wt.-%, most preferably from 0.1 to 1 wt.-%, relative to the total weight of said mixture or product.

According to another preferred embodiment, the weight ratio between the two fatty acid esters as defined herein comprised in the mixture or product as defined herein is from 10:1 to 1:10, more preferably from 5:1 to 1:5 and most preferably from 3:1 to 1:3.

Advantageously, mixtures and products comprising binary combinations of fatty acid esters of caprylic acid and of fatty acid esters of undecylenic acid as defined above display particularly high antimicrobial activity against *Malassezia* (as will be demonstrated further below).

According to an alternative embodiment, the present invention relates to a mixture, preferably product selected from the group consisting of leave-on skin care product, preferably oil in water emulsion or water in oil emulsion, and rinse-off skin care product, preferably shampoo, more preferably anti-dandruff shampoo, comprising a fatty acid ester or mixture of two or more fatty acid esters or mixture comprising one or more fatty acid esters, wherein the fatty acid ester or one, two, three or more, preferably all, of the fatty acid ester(s) is/are selected from the group consisting of 3-hydroxypropyl caprylate, glyceryl monocaprylate, 3-hydroxypropyl undecylenate and glyceryl monoundecylenate, preferably wherein the fatty acid ester or one, two or three, preferably all, of the fatty acid ester(s) is/are selected from the group consisting of 3-hydroxypropyl caprylate, glyceryl monocaprylate and 3-hydroxypropyl undecylenate, more preferably wherein the fatty acid ester or one or two, preferably all, of the fatty acid ester(s) is/are selected from the group consisting of 3-hydroxypropyl caprylate and 3-hydroxypropyl undecylenate.

According to a preferred alternative embodiment, the present invention relates to a mixture, preferably product selected from the group consisting of leave-on skin care product, preferably oil in water emulsion or water in oil emulsion, and rinse-off skin care product, preferably shampoo, more preferably anti-dandruff shampoo, comprising 3-hydroxypropyl caprylate, glyceryl monocaprylate and 3-hydroxypropyl undecylenate.

According to a particularly preferred alternative embodiment, the present invention relates to a mixture, preferably product selected from the group consisting of leave-on skin care product, preferably oil in water emulsion or water in oil emulsion, and rinse-off skin care product, preferably shampoo, more preferably anti-dandruff shampoo, comprising 3-hydroxypropyl caprylate, glyceryl monocaprylate, 3-hydroxypropyl undecylenate and glyceryl monoundecylenate.

A preferred embodiment relates to a mixture or product as defined herein, further comprising one or more 1,2-alkane diol(s), preferably one or more 1,2-alkane diol(s) selected from the group consisting of 1,2-pentanediol, 1,2-hexanediol, 1,2-octanediol and 1,2-decanediol, more preferably one 1,2-alkane diol selected from the group consisting of 1,2-pentanediol, 1,2-hexanediol, 1,2-octanediol and 1,2-decanediol.

According to a preferred embodiment, the total amount of the fatty acid ester(s) (as defined herein) and 1,2-alkane diol(s) (as defined herein) comprised in the mixture or product as defined herein is from 0.1 to 10 wt.-%, more preferably from 0.2 to 5 wt.-%, most preferably from 0.3 to 3 wt.-%, relative to the total weight of said mixture or product.

According to another preferred embodiment, the weight ratio between the fatty acid ester(s) (as defined herein) and the 1,2-alkane diol(s) (as defined herein) comprised in the mixture or product as defined herein is from 20:1 to 1:20, more preferably from 10:1 to 1:10 and most preferably from 5:1 to 1:5.

Another preferred embodiment relates to a mixture, preferably a product selected from the group consisting of leave-on skin care product, preferably oil in water emulsion or water in oil emulsion, and rinse-off skin care product, preferably shampoo, more preferably anti-dandruff shampoo, comprising 1,2-pentanediol and 3-hydroxypropyl caprylate, or comprising 1,2-pentanediol and 3-hydroxypropyl undecylenate, or comprising 1,2-hexanediol and 3-hydroxypropyl caprylate, or comprising 1,2-hexanediol and 3-hydroxypropyl undecylenate, or comprising 1,2-octanediol and 3-hydroxypropyl caprylate, or comprising 1,2-octanediol and 3-hydroxypropyl undecylenate, or comprising 1,2-decanediol and 3-hydroxypropyl caprylate, or comprising 1,2-decanediol and 3-hydroxypropyl undecylenate, or comprising 1,2-pentanediol and glyceryl monocaprylate, or comprising 1,2-pentanediol and glyceryl monoundecylenate, or comprising 1,2-hexanediol and glyceryl monocaprylate, or comprising 1,2-hexanediol and glyceryl monoundecylenate, or comprising 1,2-octanediol and glyceryl monocaprylate, or comprising 1,2-octanediol and glyceryl monoundecylenate, or comprising 1,2-decanediol and glyceryl monocaprylate, or comprising 1,2-decanediol and glyceryl monoundecylenate.

It was surprisingly found that the addition of an 1,2-alkane diol as defined herein to a caprylic acid ester or undecylenic acid ester as defined herein leads to a synergistic increase in antimicrobial activity against *Malassezia*. Thus, the mixtures or products as defined herein display particularly high antimicrobial activity against *Malassezia* (as will be demonstrated further below).

Another preferred embodiment of the invention relates to a mixture or product as defined herein, comprising one or more additional active agent(s), preferably one or more antimicrobial agent(s), more preferably one or more active agent(s) selected from the group consisting of clotrimazole, bifonazole, miconazole, ketoconazole, fluconazole, climbazole, itraconazole, terbinafine, nystatin, amorolfine, ciclopirox, octopirox and undecylenic acid.

Another aspect of the present invention relates to a mixture or product as defined herein for use in the treatment of an excess of *Malassezia* on the skin surface, preferably on the scalp, of mammals, preferably of humans.

As defined above, an excess of *Malassezia* on the skin surface, preferably on the scalp, of mammals, preferably of humans, relates to a situation where the total amount of *Malassezia* cells present on said skin surface leads to symptoms of skin disease such as, for example, redness, itching, dryness, flaking, greasiness, hypopigmentation and/or hyperpigmentation of the skin.

A preferred embodiment relates to a mixture or product for use as defined herein, wherein *Malassezia* is/are one or more species selected from the group consisting of *M. furfur, M. pachydermatis, M. sympodialis, M. globosa, M. obtusa, M. restricta, M. slooffiae, M. dermatis, M. japonica, M. nana, M. yamatoensis, M. caprae, M. equina, M. cuniculi, M. brasiliensis, M. psitaci* and *M. arunalokei*, preferably is/are selected from the group consisting of *M. restricta, M. globosa, M. furfur, M. sympodialis* and *M. dermatis*.

Another preferred embodiment of the invention relates to a mixture or product for use as defined herein, comprising one or more additional active agent(s), preferably one or more antimicrobial agent(s), more preferably one or more active agent(s) selected from the group consisting of clotrimazole, bifonazole, miconazole, ketoconazole, fluconazole, climbazole, itraconazole, terbinafine, nystatin, amorolfine, ciclopirox, octopirox and undecylenic acid.

Another aspect of the present invention relates to a fatty acid ester or a mixture of two or more fatty acid esters or a mixture comprising one or more fatty acid esters, wherein the fatty acid ester or one, two, three or more, preferably all, of the fatty acid ester(s) is/are selected from the group consisting of 3-hydroxypropyl caprylate, glyceryl monocaprylate, 3-hydroxypropyl undecylenate and glyceryl monoundecylenate, preferably wherein the fatty acid ester or one, two or three, preferably all, of the fatty acid ester(s) is/are selected from the group consisting of 3-hydroxypropyl caprylate, glyceryl monocaprylate and 3-hydroxypropyl undecylenate, more preferably wherein the fatty acid ester or one or two, preferably all, of the fatty acid ester(s) is/are selected from the group consisting of 3-hydroxypropyl caprylate and 3-hydroxypropyl undecylenate, or a mixture or product as defined above for avoiding dandruff and/or for reducing the amount of dandruff on human skin, preferably on human scalp.

Within the framework of the present text, the term "avoiding dandruff on human skin, preferably on human scalp" relates to a preventive measure where the first occurrence or reoccurrence of dandruff on a defined area of human skin, preferably of human scalp, is avoided by applying the fatty acid esters or mixtures as defined herein once or repeatedly to said defined area of human skin. As a result, no dandruff is visible on said defined area of the human skin when inspected (by a trained professional in the field, such as e.g. a dermatologist) by naked human eye.

Within the framework of the present text, the term "reducing the amount of dandruff on human skin, preferably on human scalp" relates to a measure where the total amount of dandruff on a defined area of human skin, preferably of human scalp, as observed (by a trained professional in the field) by naked human eye is reduced by more than 10, 20, 30, 50, 60, 70, 80 or 90% after one-off or repeated treatment of said defined area with the fatty acid esters or mixtures as defined herein.

A preferred embodiment relates to 3-hydroxypropyl caprylate or glyceryl monocaprylate or 3-hydroxypropyl undecylenate or glyceryl monoundecylenate or to a mixture comprising 3-hydroxypropyl caprylate or glyceryl monocaprylate or 3-hydroxypropyl undecylenate or glyceryl monoundecylenate (as the only *Malassezia*-active ingredient in the mixture) for avoiding dandruff and/or for reducing the amount of dandruff on human skin, preferably on human scalp.

Another preferred embodiment of the present invention relates to a mixture of 3-hydroxypropyl caprylate and 3-hydroxypropyl undecylenate, or of glyceryl monocaprylate and 3-hydroxypropyl undecylenate, or of 3-hydroxypropyl caprylate and glyceryl monoundecylenate, or of glyceryl monocaprylate and glyceryl monoundecylenate, or of 3-hydroxypropyl caprylate and glyceryl monocaprylate, or to a mixture comprising 3-hydroxypropyl caprylate and 3-hydroxypropyl undecylenate, or glyceryl monocaprylate and 3-hydroxypropyl undecylenate, or 3-hydroxypropyl caprylate and glyceryl monoundecylenate, or glyceryl monocaprylate and glyceryl monoundecylenate, or 3-hydroxypropyl caprylate and glyceryl monocaprylate (as the only

*Malassezia*-active ingredients in the mixture) for avoiding dandruff and/or for reducing the amount of dandruff on human skin, preferably on human scalp.

Another preferred embodiment of the present invention relates to a mixture of 3-hydroxypropyl caprylate, glyceryl monocaprylate and 3-hydroxypropyl undecylenate, or to a mixture comprising 3-hydroxypropyl caprylate, glyceryl monocaprylate and 3-hydroxypropyl undecylenate (as the only *Malassezia*-active ingredients in the mixture) for avoiding dandruff and/or for reducing the amount of dandruff on human skin, preferably on human scalp.

Another preferred embodiment of the present invention relates to a mixture of 3-hydroxypropyl caprylate, glyceryl monocaprylate, 3-hydroxypropyl undecylenate and glyceryl monoundecylenate, or to a mixture comprising 3-hydroxypropyl caprylate, glyceryl monocaprylate, 3-hydroxypropyl undecylenate and glyceryl monoundecylenate (as the only *Malassezia*-active ingredients in the mixture) for avoiding dandruff and/or for reducing the amount of dandruff on human skin, preferably on human scalp.

Another preferred embodiment of the invention relates to a fatty acid ester or mixture of two or more fatty acid esters or mixture comprising one or more fatty acid esters, wherein the fatty acid ester or one, two or three, preferably all, of the fatty acid ester(s) is/are selected from the group consisting of 3-hydroxypropyl caprylate, 3-hydroxypropyl undecylenate and glyceryl monoundecylenate for avoiding dandruff and/or for reducing the amount of dandruff on human skin, preferably on human scalp.

More preferably, fatty acid esters and mixtures for use according to the invention (further) are not or do not comprise any diesters of caprylic acid and/or are not or do not comprise any triesters of caprylic acid are not or do not comprise any ethoxylated variants of caprylic acid and/or are not or do not comprise any diesters of undecylenic acid and/or are not or do not comprise any triesters of undecylenic acid and/or are not or do not comprise any ethoxylated variants of undecylenic acid.

Another preferred embodiment relates to a mixture for use as defined above, wherein the mixture comprising one or more fatty acid esters is a product selected from the group consisting of leave-on skin care product, preferably oil in water emulsion or water in oil emulsion, and rinse-off skin care product, preferably shampoo, more preferably anti-dandruff shampoo.

Another preferred embodiment of the present invention relates to a mixture for use as defined herein, comprising one or more additional active agent(s), preferably one or more antimicrobial agent(s), more preferably one or more active agent(s) selected from the group consisting of clotrimazole, bifonazole, miconazole, ketoconazole, fluconazole, climbazole, itraconazole, terbinafine, nystatin, amorolfine, ciclopirox, octopirox and undecylenic acid.

A preferred alternative embodiment relates to a fatty acid ester for use as defined herein, which is used in combination with one or more additional active agent(s), preferably with one or more antimicrobial agent(s), more preferably with one or more active agent(s) selected from the group consisting of clotrimazole, bifonazole, miconazole, ketoconazole, fluconazole, climbazole, itraconazole, terbinafine, nystatin, amorolfine, ciclopirox, octopirox and undecylenic acid.

Another aspect of the present invention relates to the cosmetic, non-therapeutic use of a fatty acid ester or of a mixture of two or more fatty acid esters or of a mixture comprising one or more fatty acid esters, wherein the fatty acid ester or one, two, three or more, preferably all, of the fatty acid ester(s) is/are selected from the group consisting of 3-hydroxypropyl caprylate, glyceryl monocaprylate, 3-hydroxypropyl undecylenate and glyceryl monoundecylenate, preferably wherein the fatty acid ester or one, two or three, preferably all, of the fatty acid ester(s) is/are selected from the group consisting of 3-hydroxypropyl caprylate, glyceryl monocaprylate and 3-hydroxypropyl undecylenate, more preferably wherein the fatty acid ester or one or two, preferably all, of the fatty acid ester(s) is/are selected from the group consisting of 3-hydroxypropyl caprylate and 3-hydroxypropyl undecylenate, or of a mixture or product as defined above to reduce the amount of *Malassezia* on the skin surface, preferably on the scalp, of mammals, preferably of humans and/or to avoid dandruff and/or to reduce the amount of dandruff on human skin, preferably on human scalp.

As defined above, an excess of *Malassezia* on the skin surface of mammals, preferably of humans, relates to a situation where the total amount of *Malassezia* cells present on said skin surface leads to symptoms of skin disease such as, for example, redness, itching, dryness, flaking, greasiness, hypopigmentation and/or hyperpigmentation of the skin.

However, it may also be desirable to use the fatty acid ester(s) or mixtures as defined herein cosmetically/non-therapeutically to reduce the total amount of *Malassezia* cells on the skin surface, preferably on the scalp, of mammals, preferably of humans, in particular before a severe skin disease as described above develops. It is, for example, possible to use the fatty acid ester(s) or mixtures as defined herein to improve light symptoms of redness, itching, dryness, flaking, greasiness, hypopigmentation and/or hyperpigmentation of the skin, that would not (yet) be categorized as skin disease.

The term "to reduce the amount of *Malassezia* on the skin surface" as used within the present text is defined as a significant reduction of the total number of *Malassezia* cells on a defined area of skin surface of a mammal, preferably of a human, i.e. preferably a reduction of more than 10, 20, 30, 40, 50, 60, 70, 80 or 90% of the total number of *Malassezia* cells on a defined area of skin surface.

Within the framework of the present text, the term "to avoid dandruff on human skin, preferably on human scalp" relates to a preventive measure where the first occurrence or reoccurrence of dandruff on a defined area of human skin, preferably of human scalp, is avoided by applying the fatty acid esters or mixtures as defined herein once or repeatedly to said defined area of human skin. As a result, no dandruff is visible on said defined area of the human skin when inspected (by a trained professional in the field, such as e.g. a dermatologist) by naked human eye.

Within the framework of the present text, the term "to reduce the amount of dandruff on human skin, preferably on human scalp" relates to a measure where the total amount of dandruff on a defined area of human skin, preferably of human scalp, as observed (by a trained professional in the field) by naked human eye is reduced by more than 10, 20, 30, 50, 60, 70, 80 or 90% after one-off or repeated treatment of said defined area with the fatty acid esters or mixtures as defined herein.

Another embodiment of the invention relates to the cosmetic, non-therapeutic use as defined herein, wherein additionally to the fatty acid ester or to the mixture of two or more fatty acid esters or to the mixture comprising one or more fatty acid esters one or more 1,2-alkane diol(s), preferably of one or more 1,2-alkane diol(s) selected from the group consisting of 1,2-pentanediol, 1,2-hexanediol, 1,2-octanediol and 1,2-decanediol, more preferably one 1,2-alkane diol selected from the group consisting of 1,2-pentanediol, 1,2-hexanediol, 1,2-octanediol and 1,2-decanediol, are used.

As outlined above, it was surprisingly found that the addition of an 1,2-alkane diol as defined herein to a caprylic acid ester or undecylenic acid ester as defined herein leads to a synergistic increase in antimicrobial activity against *Malassezia*.

Thus, another preferred embodiment of the invention relates to the cosmetic, non-therapeutic use of a mixture comprising 1,2-pentanediol and 3-hydroxypropyl caprylate, or comprising 1,2-pentanediol and 3-hydroxypropyl undecylenate, or comprising 1,2-hexanediol and 3-hydroxypropyl caprylate, or comprising 1,2-hexanediol and 3-hydroxypropyl undecylenate, or comprising 1,2-octanediol and 3-hydroxypropyl caprylate, or comprising 1,2-octanediol and 3-hydroxypropyl undecylenate, or comprising 1,2-decanediol and 3-hydroxypropyl caprylate, or comprising 1,2-decanediol and 3-hydroxypropyl undecylenate, or comprising 1,2-pentanediol and glyceryl monocaprylate, or comprising 1,2-pentanediol and glyceryl monoundecylenate, or comprising 1,2-hexanediol and glyceryl monocaprylate, or comprising 1,2-hexanediol and glyceryl monoundecylenate, or comprising 1,2-octanediol and glyceryl monocaprylate, or comprising 1,2-octanediol and glyceryl monoundecylenate, or comprising 1,2-decanediol and glyceryl monocaprylate, or comprising 1,2-decanediol and glyceryl monoundecylenate, to reduce the amount of *Malassezia* on the skin surface, preferably on the scalp, of mammals, preferably of humans.

Another embodiment of the invention relates to the cosmetic, non-therapeutic use as defined herein, wherein *Malassezia* is/are one or more species selected from the group consisting of *M. furfur, M. pachydermatis, M. sympodialis, M. globosa, M. obtusa, M. restricta, M. slooffiae, M. dermatis, M. japonica, M. nana, M. yamatoensis, M. caprae, M. equina, M. cuniculi, M. brasiliensis, M. psitaci* and *M. arunalokei*, preferably is/are selected from the group consisting of *M. restricta, M. globosa, M. furfur, M. sympodialis* and *M. dermatis*.

Another embodiment of the invention relates to the cosmetic, non-therapeutic use as defined herein, wherein the mixture comprising one or more fatty acid esters is a product selected from the group consisting of leave-on skin care product, preferably oil in water emulsion or water in oil emulsion, and rinse-off skin care product, preferably shampoo, more preferably anti-dandruff shampoo.

Another embodiment of the invention relates to the cosmetic, non-therapeutic use as defined herein, wherein additionally to the fatty acid ester or to the mixture of two or more fatty acid esters or to the mixture comprising one or more fatty acid esters and, optionally to the one or more 1,2-alkane diol(s), one or more additional active agent(s), preferably one or more antimicrobial agent(s), more preferably one or more active agent(s) selected from the group consisting of clotrimazole, bifonazole, miconazole, ketoconazole, fluconazole, climbazole, itraconazole, terbinafine, nystatin, amorolfine, ciclopirox, octopirox and undecylenic acid is/are used.

A method for reducing the amount of *Malassezia* on the skin surface, preferably on the scalp, of mammals, preferably of humans, in particular of humans in need thereof (i.e. of humans showing one or more symptoms of skin disease such as, for example, redness, itching, dryness, flaking, greasiness, hypopigmentation and/or hyperpigmentation of the skin) comprising or consisting of the step of applying a fatty acid ester or a mixture of two or more fatty acid esters or a mixture comprising one or more fatty acid esters, wherein the fatty acid ester or one, two, three or more, preferably all, of the fatty acid ester(s) is/are selected from the group consisting of 3-hydroxypropyl caprylate, glyceryl monocaprylate, 3-hydroxypropyl undecylenate and glyceryl monoundecylenate, or of applying a mixture or product as defined herein to the skin surface, preferably to the scalp, of a mammal, preferably of a human, is also disclosed within the framework of the present text.

A preferred embodiment relates to a method as defined above, wherein the applied fatty acid ester or one, two or three, preferably all, of the fatty acid ester(s) is/are selected from the group consisting of 3-hydroxypropyl caprylate, glyceryl monocaprylate and 3-hydroxypropyl undecylenate.

Another preferred embodiment relates to a method as defined above, wherein the applied fatty acid ester or one, two or three, preferably all, of the fatty acid ester(s) is/are selected from the group consisting of 3-hydroxypropyl caprylate, 3-hydroxypropyl undecylenate and glyceryl monoundecylenate.

Another preferred embodiment relates to a method as defined above, wherein the applied fatty acid ester or one or two, preferably all, of the fatty acid ester(s) is/are selected from the group consisting of 3-hydroxypropyl caprylate and 3-hydroxypropyl undecylenate.

Another preferred embodiment relates to a method as defined above, wherein the applied fatty acid ester is 3-hydroxypropyl caprylate or glyceryl monocaprylate or 3-hydroxypropyl undecylenate or glyceryl monoundecylenate or wherein the applied mixture comprises 3-hydroxypropyl caprylate or glyceryl monocaprylate or 3-hydroxypropyl undecylenate or glyceryl monoundecylenate (as the only *Malassezia*-active ingredient in the mixture).

Another preferred embodiment relates to a method as defined above, wherein the applied mixture is 3-hydroxypropyl caprylate and 3-hydroxypropyl undecylenate, or is glyceryl monocaprylate and 3-hydroxypropyl undecylenate, or is 3-hydroxypropyl caprylate and glyceryl monoundecylenate, or is glyceryl monocaprylate and glyceryl monoundecylenate, or is 3-hydroxypropyl caprylate and glyceryl monocaprylate, or wherein the applied mixture comprises 3-hydroxypropyl caprylate and 3-hydroxypropyl undecylenate, or comprises glyceryl monocaprylate and 3-hydroxypropyl undecylenate, or comprises 3-hydroxypropyl caprylate and glyceryl monoundecylenate, or comprises glyceryl monocaprylate and glyceryl monoundecylenate, or comprises 3-hydroxypropyl caprylate and glyceryl monocaprylate (as the only *Malassezia*-active ingredients in the mixture).

Another preferred embodiment relates to a method as defined above, wherein the applied mixture is 3-hydroxypropyl caprylate, glyceryl monocaprylate and 3-hydroxypropyl undecylenate, or wherein the applied mixture comprises 3-hydroxypropyl caprylate, glyceryl monocaprylate and 3-hydroxypropyl undecylenate (as the only *Malassezia*-active ingredients in the mixture).

Another preferred embodiment relates to a method as defined above, wherein the applied mixture is 3-hydroxypropyl caprylate, glyceryl monocaprylate, 3-hydroxypropyl undecylenate and glyceryl monoundecylenate, or wherein the applied mixture comprises 3-hydroxypropyl caprylate, glyceryl monocaprylate, 3-hydroxypropyl undecylenate and glyceryl monoundecylenate (as the only *Malassezia*-active ingredients in the mixture).

More preferably, the applied fatty acid esters or mixtures in the method as defined above (further) are not or do not comprise any diesters of caprylic acid and/or are not or do not comprise any triesters of caprylic acid are not or do not comprise any ethoxylated variants of caprylic acid and/or are not or do not comprise any diesters of undecylenic acid and/or are not or do not comprise any triesters of undecylenic acid and/or are not or do not comprise any ethoxylated variants of undecylenic acid.

Another embodiment relates to a method as defined above, wherein Malassezia is/are one or more species selected from the group consisting of M. furfur, M. pachydermatis, M. sympodialis, M. globosa, M. obtusa, M. restricta, M. slooffiae, M. dermatis, M. japonica, M. nana, M. yamatoensis, M. caprae, M. equina, M. cuniculi, M. brasiliensis, M. psitaci and M. arunalokei, preferably is/are selected from the group consisting of M. restricta, M. globosa, M. furfur, M. sympodialis and M. dermatis.

Another embodiment relates to a method as defined above, wherein the mixture comprising one or more fatty acid esters is a product selected from the group consisting of leave-on skin care product, preferably oil in water emulsion or water in oil emulsion, and rinse-off skin care product, preferably shampoo, more preferably anti-dandruff shampoo.

Another embodiment relates to a method as defined above, wherein the applied mixture or product as defined herein comprises one or more additional active agent(s), preferably one or more antimicrobial agent(s), more preferably one or more active agent(s) selected from the group consisting of clotrimazole, bifonazole, miconazole, ketoconazole, fluconazole, climbazole, itraconazole, terbinafine, nystatin, amorolfine, ciclopirox, octopirox and undecylenic acid.

A preferred alternative embodiment relates to a method as defined above, wherein the fatty acid ester as defined herein is applied in combination with one or more additional active agent(s), preferably with one or more antimicrobial agent(s), more preferably with one or more active agent(s) selected from the group consisting of clotrimazole, bifonazole, miconazole, ketoconazole, fluconazole, climbazole, itraconazole, terbinafine, nystatin, amorolfine, ciclopirox, octopirox and undecylenic acid.

(Preferred) embodiments of the fatty acid esters or mixtures or products for use according to the invention correspond to or can be derived from the (preferred) embodiments of the mixtures or products or uses according to the invention or from the (preferred) embodiments of the method as described herein, which are explained above, or vice versa.

The invention will now be described in more detail hereinafter with references to selected examples.

EXAMPLES

1. Microbial Test Strains

The fatty acid esters and their mixtures were tested for growth inhibition against Malassezia. The following reference strains were included:

TABLE 1

| CBS = Centraalbureau voor Schimmelcultures, Utrecht, NI; The M. globosa wildtype strain PM1 was isolated and maintained by Prof. P. Mayser, JLU Giessen. | |
| --- | --- |
| M. furfur | CBS 1878, CBS 7019 |
| M. sympodialis | CBS 7222, CBS 7979, ATCC 42132, DSM 6171 |

TABLE 1-continued

| CBS = Centraalbureau voor Schimmelcultures, Utrecht, NI; The M. globosa wildtype strain PM1 was isolated and maintained by Prof. P. Mayser, JLU Giessen. | |
| --- | --- |
| M. globosa | CBS 7966, PM1, CBS 7705 |
| M. restricta | CBS 7877 |
| M. pachydermatis | CBS 1879, 1892 |

2. Preparation of Test Plates

Tests were performed on solid media using agar dilution tests. Stock solutions of test substances were prepared in mDixon-Agar (cf. Table 2). Lower test concentrations were obtained by diluting stock solutions with fresh agar.

Preparation of liquid agar was carried out in temperated water bath. Required amounts of test substances were weighed in 130 ml of Dixon Agar and mixed with fresh Dixon-Agar to reach desired concentrations of test substances. Agar solutions with test substances were then poured into 24 well-plates. The pH value in all assays was maintained at 5.5. Preparation of test substances was done on weight per volume base. All results are expressed in parts per million (1 ppm=0.0001%).

TABLE 2

| Composition of mDixon-Agar (for 350 ml) | |
| --- | --- |
| Malt extract-bouillon | 12.6 g |
| Peptone (Casein) | 3.5 g |
| Ox gall | 7.0 g |
| Agar | 7.0 g |
| Cycloheximide | 175 mg |
| Chloramphenicol | 175 mg |
| Tween 40 | 3.5 ml |
| Olive oil | 0.7 ml |
| Glycerol | 0.7 ml |

3. Inoculation of Test Strains

Microbial test strains were prepared according to the procedure described by Mayser (Mayser P., Medium chain fatty acid ethyl esters—activation of antimicrobial effects by Malassezia enzymes. Mycoses 2015; 58:215-9). Briefly, Malassezia strains were cultivated on selective agar for pathogenic fungi (Merck) and overlaid with a thin layer of cold-sterilized olive oil. Cell counts were determined in a Neubauer chamber and $1.75 \times 10^6$ cells suspended in 20 μl olive oil transferred to the test plates (corresponds to $10^6$ cells per $cm^2$). Incubation was carried out at 32° C. over a maximal duration of 14 days with regular inspection and documentation of growth status. Minimal inhibitory concentrations (MICs) were determined as the lowest concentrations of test compound without visible growth. Each experiment was repeated to confirm results.

4. Results 4.1. Antifungal Activity

Minimal inhibitory concentrations for test substances were determined for the different test strains (Table 3, 4, 5). As reference substances, the pure acids caprylic acid and undecylenic acid were used.

TABLE 3

Minimal inhibitory concentrations (MICs) against *Malassezia* test strains (the term "test substance" relates to the compounds listed in the column underneath; the numbers in the row to the right of the term "test substance" relate to the respective *Malassezia* test strains)

| | Strain | | | | | | | | | | | |
|---|---|---|---|---|---|---|---|---|---|---|---|---|
| | *M. furfur* | | *M. sympodialis* | | | | *M. globosa* | | | *M. restricta* | *M. pachydermatis* | |
| Test substance | 1878 | 7019 | 7222 | 7979 | 42132 | 6171 | 7966 | PM1 | 7705 | 7877 | 1879 | 1892 |
| Caprylic acid | 1000 | 2000 | 330 | 1000 | 330 | 500 | 1000 | 500 | n.d. | 200 | 100 | 200 |
| Ethyl caprylate | >20000 | 10000 | 1000 | 1000 | 1000 | 1000 | 1000 | 1000 | n.d. | 4000 | <500 | 1000 |
| 3-Hydroxypropyl caprylate | 2000 | 2000 | 1000 | 2000 | 1000 | 2000 | 1000 | 500 | 1000 | 1000 | 330 | 500 |
| Glyceryl monocaprylate | 4000 | 4000 | 1000 | 1000 | 1000 | 2000 | 1000 | 500-1000 | 1000 | 330 | 330 | 500 |
| Undecylenic acid | 2000 | >2000 | 100 | 200 | 100 | 100 | 2000 | 677 | 330 | 500 | 1000 | 500 |
| Ethyl undecylenoate | 20000 | >20000 | 200 | 200 | 200 | 200 | 10000 | 8000 | 4000 | 1000 | 2000 | 500 |
| 3-Hydroxypropyl undecylenoate | 8000 | 8000 | 4000 | 1000 | 2000 | 2000 | 2000 | 2000 | 1000 | 1000 | 2000 | 1000 |
| Glyceryl monoundecylenoate | 8000 | 8000 | 500 | 500 | 500 | 200 | 2000 | 2000 | 1000 | 1000 | 8000 | 4000 |

The results in Table 3 demonstrate that monoesters of caprylic and undecylenic acid with either 1,3-propanediol or glycerol are highly active against a broad spectrum of *Malassezia* strains inhabiting human and animal skin.

TABLE 4

Minimal inhibitory concentrations (MICs) against *Malassezia* test strains (the term "test substance" relates to the compounds listed in the column underneath; the numbers in the row to the right of the term "test substance" relate to the respective *Malassezia* test strains)

| | Strain | | | | | | | | | | | |
|---|---|---|---|---|---|---|---|---|---|---|---|---|
| | *M. furfur* | | *M. sympodialis* | | | | *M. globosa* | | | *M. restricta* | *M. pachydermatis* | |
| Test substance | 1878 | 7019 | 7222 | 7979 | 42132 | 6171 | 7966 | PM1 | 7705 | 7877 | 1879 | 1892 |
| 3-Hydroxypropyl dicaprylate | >20000 | 20000 | 20000 | 20000 | 4000 | 20000 | 8000 | 8000 | n.d. | n.d. | n.d. | n.d. |
| PEG9-caprylate | 20000 | 10000 | 10000 | 8000 | 10000 | 8000 | 2000 | 2000 | n.d. | 2000 | 2000 | 4000 |

The results in Table 4 show that diesters or ethoxylated variants of caprylic acid are not or only partially active against *Malassezia* strains.

TABLE 5

Minimal inhibitory concentrations (MICs) against *Malassezia* test strains (the term "test substance" relates to the compounds listed in the column underneath; the numbers in the row to the right of the term "test substance" relate to the respective *Malassezia* test strains)

| | Strain | | | | | | | |
|---|---|---|---|---|---|---|---|---|
| | *M. furfur* | | *M. globosa* | | | *M. restricta* | *M. pachydermatis* | |
| Test substance | 1878 | 7019 | 7966 | PM1 | 7705 | 7877 | 1879 | 1892 |
| 3-Hydroxypropyl diundecylenoate | >20000 | >20000 | 10000 | 10000 | n.d. | n.d. | n.d. | n.d. |
| Glyceryl triundecylenoate | 10000 | >20000 | >20000 | 8000 | 8000 | 4000 | 4000 | 4000 |
| PEG-9-undecylenoate | 20000 | >20000 | 10000 | 8000 | n.d. | 4000 | 8000 | 8000 |

The results in Table 5 show that diesters, triesters or ethoxylated variants of undecylenic acid are not or only partially active against *Malassezia* strains.

Additionally, MIC-values for various alkane diols were determined (Table 6).

TABLE 6

Minimal inhibitory concentrations (MICs) for alkane diols against *Malassezia* test strains (the term "test substance" relates to the compounds listed in the column underneath; the numbers in the row to the right of the term "test substance" relate to the respective *Malassezia* test strains)

| | Strain | | | | | | | |
|---|---|---|---|---|---|---|---|---|
| | *M. sympodialis* | | | | *M. globosa* | | | *M. restricta* |
| Test substance | 7222 | 7979 | 42132 | 6171 | 7966 | PM1 | 7705 | 7877 |
| 1,3-Propandiol | 33000 | 80000 | 40000 | 80000 | 40000 | 33000 | 80000 | 33000 |
| 1,2-Pentandiol | 20000 | 20000 | 20000 | 20000 | 10000 | 10000 | 20000 | 10000 |
| 1,2-Hexandiol | 10000 | 10000 | 10000 | 10000 | 5000 | 5000 | 10000 | 5000 |
| 1,2-Octandiol | 2000 | 2000 | 2000 | 2000 | 2000 | 2000 | 4000 | 1000 |
| 1,2-Decandiol | 1000 | 2000 | 1000 | 4000 | 8000 | 8000 | 8000 | 1000 |
| 1,2-Dodecandiol | 4000 | 4000 | 2000 | 4000 | 40000 | 40000 | 40000 | 8000 |

Subsequently, binary mixtures of caprylic acid and undecylenic acid esters were prepared (Table 7) and MIC-values determined as described above (Table 8).

Synergistic antimicrobial effects were determined by calculation of Synergy Indices (SI) according to Kull's equation (I) (Kull, F. C., Eismann, P. C., Sylvestrowicz, H. D., and R. L. Mayer (1961). Mixtures of Quaternary Ammonium Compounds and Long-chain Fatty Acids as Antifungal Agents. Applied Microbiology 9, 538-541. Steinberg, D. C. (2000). Measuring Synergy. Cosmetics & Toiletries 115 (11), 59-62).

$$SI = (C_{mixture} \times P_A)/C_A + (C_{mixture} \times P_B)/C_B \quad (I)$$

where
SI is the Synergy Index according to Kull
$C_A$ is the cell count for substance A
$C_B$ is the cell count for substance B
$C_{mixture}$ is the cell count for the mixture of substances A and B
$P_A$ is the proportion of the substance A in the mixture
$P_B$ is the proportion of the substance B in the mixture.

SI-values below 1 indicate synergistic activity of test substances.

TABLE 7

Binary mixtures of caprylic acid and undecylenic acid esters including ratios tested

| Designation of mixture | Ratio of test substances | Test substance |
|---|---|---|
| 1a | 1:1 | 3-Hydroxypropyl caprylate/ |
| 1b | 1:2 | glyceryl monoundecylenate |
| 1c | 2:1 | |
| 2a | 1:1 | 3-Hydroxypropyl caprylate/ethyl |
| 2b | 1:2 | undecylenate |
| 2c | 2:1 | |
| 3a | 1:1 | 3-Hydroxypropyl undecylenate/ |
| 3b | 1:2 | glyceryl monocaprylate |
| 3c | 2:1 | |
| 4a | 1:1 | 3-Hydroxypropyl caprylate/3- |
| 4b | 1:2 | hydroxypropyl undecylenate |
| 4c | 2:1 | |

TABLE 8

Minimal inhibitory concentrations (MICs) for binary mixtures of caprylic acid and undecylenic acid esters against *Malassezia* test strains and calculated SI-indices (the term "test mixture" relates to the mixtures listed in the column underneath; the numbers in the row to the right of the term "test mixture" relate to the respective *Malassezia* test strains)

| | | Strain | | | | | | | | | | |
|---|---|---|---|---|---|---|---|---|---|---|---|---|
| | | *M. furfur* | | *M. sympodialis* | | | | *M. globosa* | | | *M. restricta* | *M. pachydermatis* |
| Test mixture | | 1878 | 7019 | 7222 | 7979 | 42132 | 6171 | 7966 | PM1 | 7705 | 7877 | 1879 | 1892 |
| 1a | | 20000 | 4000 | 1000 | 1000 | 500 | 330 | 1000 | 1000 | 1000 | 330 | 500 | 500 |
| SI | | 6.25 | 1.20 | 1.50 | 1.25 | 0.75 | 0.91 | 0.75 | 1.25 | 1.00 | 0.33 | 0.79 | 0.56 |
| 1b | | n.d. | n.d. | 200 | 200 | <100[1] | 200 | 500 | 1000 | 1000 | 200 | n.d. | n.d. |
| SI | | n.d. | n.d. | 0.33 | 0.30 | 0.08 | 0.70 | 0.33 | 1.00 | 1.00 | 0.20 | n.d. | n.d. |
| 1c | | n.d. | n.d. | 200 | 500 | <100[1] | 330 | 500 | 330 | 500 | 200 | n.d. | n.d. |
| SI | | n.d. | n.d. | 0.26 | 0.50 | 0.07 | 0.65 | 0.41 | 0.49 | 0.50 | 0.20 | n.d. | n.d. |
| 2a | | 4000 | 4000 | 330 | 1000 | 500 | 500 | 500 | 1000 | 500 | 500 | 330 | 500 |
| SI | | 1.10 | 1.10 | 1.000 | 2.75 | 1.5 | 2.75 | 0.28 | 1.06 | 0.31 | 0.33 | 0.58 | 1.00 |
| 2b | | n.d. | n.d. | 200 | 330 | 200 | 330 | 500 | 1000 | 500 | 330 | n.d. | n.d. |
| SI | | n.d. | n.d. | 0.73 | 1.14 | 0.73 | 1.14 | 0.20 | 0.74 | 0.20 | 0.32 | n.d. | n.d. |
| 2c | | n.d. | n.d. | 330 | 1000 | 330 | 500 | 330 | 330 | 330 | 200 | n.d. | n.d. |
| SI | | n.d. | n.d. | 0.76 | 1.90 | 0.76 | 1.00 | 0.23 | 0.58 | 0.25 | 0.20 | n.d. | n.d. |

TABLE 8-continued

Minimal inhibitory concentrations (MICs) for binary mixtures of caprylic acid and undecylenic acid esters against *Malassezia* test strains and calculated SI-indices (the term "test mixture" relates to the mixtures listed in the column underneath; the numbers in the row to the right of the term "test mixture" relate to the respective *Malassezia* test strains)

| | Strain | | | | | | | | | | |
|---|---|---|---|---|---|---|---|---|---|---|---|
| | *M. furfur* | | *M. sympodialis* | | | | *M. globosa* | | | *M. restricta* | *M. pachydermatis* |
| Test mixture | 1878 | 7019 | 7222 | 7979 | 42132 | 6171 | 7966 | PM1 | 7705 | 7877 | 1879 | 1892 |
| 3a | 4000 | 4000 | 330 | 1000 | 1000 | 500 | 1000 | 1000 | 1000 | 330 | 500 | 500 |
| SI | 0.75 | 0.75 | 0.21 | 1.00 | 0.75 | 0.50 | 0.75 | 0.75 | 1.00 | 0.67 | 0.89 | 0.75 |
| 3b | n.d. | n.d. | 330 | 1000 | 330 | 1000 | 500 | 500 | 1000 | 330 | n.d. | n.d. |
| SI | n.d. | n.d. | 0.11 | 1.00 | 0.27 | 0.50 | 0.41 | 0.41 | 1.00 | 0.77 | n.d. | n.d. |
| 3c | n.d. | n.d. | 330 | 500 | 330 | 500 | 500 | 1000 | 500 | 330 | n.d. | n.d. |
| SI | n.d. | n.d. | 0.22 | 0.50 | 0.22 | 0.25 | 0.33 | 0.66 | 0.50 | 0.55 | n.d. | n.d. |
| 4a | 2000 | 4000 | 500 | 1000 | 500 | 500 | 1000 | 1000 | 1000 | 330 | 1000 | 500 |
| SI | 0.63 | 1.25 | 0.31 | 0.75 | 0.38 | 0.50 | 0.75 | 1.25 | 1.00 | 0.33 | 1.76 | 0.75 |
| 4b | n.d. | n.d. | 200 | 500 | 200 | 330 | 500 | 1000 | 1000 | 330 | n.d. | n.d. |
| SI | n.d. | n.d. | 0.10 | 0.41 | 0.13 | 0.16 | 0.21 | 0.66 | 1.00 | 0.33 | n.d. | n.d. |
| 4c | n.d. | n.d. | 330 | 1000 | 200 | 500 | 330 | 500 | 500 | 330 | n.d. | n.d. |
| SI | n.d. | n.d. | 0.14 | 0.66 | 0.20 | 0.25 | 0.22 | 0.75 | 0.50 | 0.33 | n.d. | n.d. |

[1])MIC-values <100 were set to 50 for SI-calculation

In a further experiment, binary mixtures of caprylic acid esters and undecylenic acid esters, respectively, with alkane diols were prepared (Table 9) and MIC-values determined as described above (Table 10). Synergistic antimicrobial effects were determined by calculation of Synergy Indices (SI) according to Kull's equation as described above.

TABLE 9

Binary mixtures of caprylic acid esters and undecylenic acid esters, respectively, with alkane diols including ratios tested.

| Designation of mixture | Ratio of test substances | Test substance |
|---|---|---|
| 5a | 3:1 | 1,2-Pentanediol/3-Hydroxypropyl caprylate |
| 5b | 3:1 | 1,2-Pentanediol/3-Hydroxypropyl undecylenate |
| 6a | 3:1 | 1,2-Hexanediol/3-Hydroxypropyl caprylate |
| 6b | 3:1 | 1,2-Hexanediol/3-Hydroxypropyl undecylenate |
| 7a | 2:1 | 1,2-Octanediol/3-Hydroxypropyl caprylate |
| 7b | 2:1 | 1,2-Octanediol/3-Hydroxypropyl undecylenate |
| 8a | 1:2 | 1,2-Decanediol/3-Hydroxypropyl caprylate |
| 8b | 1:2 | 1,2-Decanediol/3-Hydroxypropyl undecylenate |

TABLE 10

Minimal inhibitory concentrations (MICs) for binary mixtures of caprylic acid esters and undecylenic acid esters, respectively, with alkane diols against *Malassezia* test strains and calculated SI-indices (the term "test mixture" relates to the mixtures listed in the column underneath; the numbers in the row to the right of the term "test mixture" relate to the respective *Malassezia* test strains)

| | Strain | | | | | | | |
|---|---|---|---|---|---|---|---|---|
| | *M. sympodialis* | | | | *M. globosa* | | | *M. restricta* |
| Test mixture | 7222 | 7979 | 42132 | 6171 | 7966 | PM1 | 7705 | 7877 |
| 5a | 4000 | 4000 | 4000 | 4000 | 4000 | 4000 | 4000 | 2000 |
| SI | 1.15 | 0.65 | 1.15 | 0.65 | 1.30 | 2.30 | 1.15 | 0.65 |
| 5b | 330 | 330 | 330 | 330 | 4000 | 1000 | 4000 | 2000 |
| SI | 0.03 | 0.10 | 0.05 | 0.05 | 0.80 | 0.20 | 0.65 | 0.65 |
| 6a | 2000 | 4000 | 2000 | 4000 | 4000 | 2000 | 4000 | 2000 |
| SI | 0.65 | 0.80 | 0.65 | 0.80 | 1.60 | 1.30 | 1.30 | 0.80 |
| 6b | 330 | 330 | 500 | 500 | 2000 | 2000 | 4000 | 1000 |
| SI | 0.05 | 0.11 | 0.10 | 0.10 | 0.55 | 0.55 | 1.30 | 0.40 |
| 7a | 1000 | 2000 | 2000 | 2000 | 2000 | 2000 | 4000 | 1000 |
| SI | 0.67 | 1.00 | 1.33 | 1.00 | 1.33 | 1.00 | 2.00 | 1.00 |
| 7b | 330 | 330 | 330 | 330 | 2000 | 1000 | 4000 | 1000 |
| SI | 0.14 | 0.22 | 0.17 | 0.17 | 1.00 | 0.50 | 2.00 | 1.00 |
| 8a | 1000 | 2000 | 1000 | 1000 | 1000 | 1000 | 2000 | 1000 |

TABLE 10-continued

Minimal inhibitory concentrations (MICs) for binary mixtures of caprylic acid
esters and undecylenic acid esters, respectively, with alkane diols against *Malassezia* test
strains and calculated SI-indices (the term "test mixture" relates to the mixtures listed in the
column underneath; the numbers in the row to the right of the term "test mixture" relate to
the respective *Malassezia* test strains)

| | Strain | | | | | | | |
|---|---|---|---|---|---|---|---|---|
| | *M. sympodialis* | | | | *M. globosa* | | *M. restricta* | |
| Test mixture | 7222 | 7979 | 42132 | 6171 | 7966 | PM1 | 7705 | 7877 |
| SI | 1.00 | 1.00 | 1.00 | 0.42 | 0.71 | 1.37 | 1.42 | 1.00 |
| 8b | <100[1] | 200 | <100[1] | 330 | 2000 | 2000 | 4000 | 1000 |
| SI | 0.03 | 0.17 | 0.03 | 0.14 | 0.75 | 0.75 | 2.80 | 1.00 |

[1]MIC-values <100 were set to 50 for SI-calculation

4.2. Ester Cleavage

The two substances 3-hydroxypropyl caprylate and 3-hydroxypropyl undecylenate have shown outstanding activity against different *Malassezia* species and strains. For these two substances ester cleavage by M. globose and *M. restricta* lipases and hydrolases and subsequent liberation of free fatty acids was demonstrated.

It is well known in the art that free short- and mid-chain saturated fatty acids, for example capric acid (C10:0), caprylic acid (C8:0), and capronic acid (C6:0) show antimicrobial activity. Use of these free fatty acids for treating *Malassezia*-associated conditions and diseases in cosmetic or medical products are hampered by their intense, negatively perceived odour and their irritating potential at higher concentrations.

Surprisingly it was found that a similar antimicrobial effect can be obtained against *Malassezia* spp., but not *Candida* spp., when monoesters of these fatty acids are used. This highly specific effect is facilitated by *Malassezia* lipases and hydrolases, which cleave the esters and thereby liberate the active principle of the fatty acid. This results in a targeted activation of the antimicrobial molecules only in local areas of the skin, where *Malassezia* density is high.

For esters of monohydric alcohols, cleavage by *Malassezia* spp. has been demonstrated before. Esters of monohydric alcohols (e.g. methanol, ethanol, propanol, isopropanol etc.), however, are less active against different *Malassezia* species and also have the severe disadvantage of strong odour, which limits their use to low concentrations.

During the studies underlying the present invention, experimental proof of ester cleavage for 3-hydroxypropyl caprylate and 3-hydroxypropyl undecylenate was demonstrated for the two species *M. globosa* and *M. restricta* (cf. Table 11). These two species are the most frequently detected ones on human scalp and skin and their hydrolytic/lipolytic activities on fatty acid esters has not yet been investigated before.

TABLE 11

*Malassezia* strains used for the experiments on ester cleavage

| | |
|---|---|
| *M. restricta* | CBS* 7877 |
| *M. globosa* | CBS* 7705 |

*Reference strains of the Centraalbureau voor Schimmelcultures, Utrecht, NL

4.2.1. Method

*Malassezia* strains were cultivated on selective agar for pathogenic fungi (Merck) and overlaid with a thin layer of cold-sterilized olive oil. After 3 to 5 days, fungal cells were harvested and resuspended in the respective test substance. Cell numbers were determined using a Neubauer counting chamber (cf. Table 12). Sterile Petri dishes (diameter: 3 cm) were prepared containing selective agar for pathogenic fungi, overlaid with 100 µl of the test suspensions and incubated at 32° C.

TABLE 12

Determined *Malassezia* cell numbers per µl for each assay

| | 3-Hydroxypropyl caprylate | 3-Hydroxypropyl undecylenate |
|---|---|---|
| *M. globosa* CBS 7705 | 20500 | 26500 |
| *M. restricta* CBS 7877 | 12500 | 5550 |

After defined incubation times (0, 3, 6, 12, 24, 48, and 72 h), test suspensions were removed from the agar surface by rinsing with 1 ml chloroform and stored under cool conditions in gastight tubes until analysis. Chloroform was removed by evaporation at 30° C. in the fume hood and the remaining liquid mixed with 1 ml isopropanol, transferred in Eppendorf tubes and centrifuged. The supernatant was transferred to new Eppendorf tubes.

In order to analytically quantify esters and free fatty acid resulting from cleavage by *Malassezia* enzymes, gas chromatography was used.

For quantification (range 0.1-10 wt %) a multilevel calibration method with internal standard (ISTD, docosane [C22]; 500 mg in MtBE) was used. An equal amount of corresponding acid, ester and possible side products [0.2-50 mg/10 mL] were mixed with ISTD, diluted to an appropriate concentration and 1 µL [split1:50] was directly used for GC-analysis with the following conditions: GC Agilent 6890 with a 20 m ZB-Wax column [0.20 mm×0.20 µm], injector temperature of 250° C., detector temperature of 275° C., flow gas of 1.3 mL/min hydrogen [constant]. For temperature profile 60° C. to 240° C. with a heating rate of 9° C./min was used.

4.2.2. Results

3-Hydroxypropyl caprylate was rapidly cleaved to caprylic acid and 1,3-propanediol by the two *Malassezia* strains. With *M. globosa* CBS 7705, 75% of the ester was cleaved after 6 hours and 90% was cleaved after 12 hours (FIG. 1). On the other hand, *M. restricta* CBS 7877 was capable of cleaving 21% of the ester after 6 hours and 65% after 12 hours (FIG. 2). In assays without *Malassezia* cells, no caprylic acid was detected until the end of the experiment after 72 hours.

3-Hydroxypropyl undecylenate was accepted as a preferred substrate by *Malassezia* enzymes, as well, leading to fast generation of undecylenic acid. Incubating *M. globosa* CBS 7705 together with this substance resulted in 95% cleavage after 6 hours and 99.5% cleavage after 12 hours (FIG. 3). When *M. restricta* CBS 7877 was used, 56% cleavage was observed after 6 hours and 96% after 12 hours (FIG. 4). In assays without *Malassezia* cells, no undecylenic acid was detected until the end of the experiment after 72 hours.

5. Formulation Examples

TABLE 13

Composition of perfume oil 1 (PO1, Amounts in ‰ b.w.)

| Ingredients | Amount |
|---|---|
| ALDEHYDE C14 SO-CALLED | 2 |
| ALLYL AMYL GLYCOLATE 10% DPG | 5 |
| ANISIC ALDEHYDE PURE | 5 |
| APPLE OLIFFAC TYPE | 10 |
| Benzylacetat | 50 |
| BERGAMOT IDENTOIL ® COLOURLESS | 15 |
| CANTHOXAL | 5 |
| CETALOX 10% IPM | 3 |
| CITRONELLOL 950 | 40 |
| DAMASCENONE TOTAL 1% DPG | 5 |
| DAMASCONE ALPHA 10% DPG | 5 |
| DAMASCONE DELTA 10% DPG | 2 |
| DIMETHYL BENZYL CARBINYL BUTYRATE | 2 |
| DIPROPYLENE GLYCOL | 178 |
| EBANOL | 2 |
| ETHYL DECADIENOATE TRANS CIS-2, 4 10% IPM | 2 |
| FLOROSA | 5 |
| FRAMBINON ® 10% DPG | 7 |
| GALAXOLIDE 50% IN IPM | 100 |
| GALBEX TYPE BASE | 1 |
| GERANYL ACETATE PURE | 2 |
| HEDIONE | 30 |
| HELIOTROPIN | 10 |
| HEXENYL ACETATE CIS-3 10% DPG | 1 |
| HEXENYL SALICYLATE CIS-3 | 5 |
| HEXYL CINNAMIC ALDEHYDE ALPHA | 70 |
| HEXYL SALICYLATE | 50 |
| HYDROXY CITRONELLAL | 10 |
| ISO E SUPER | 15 |
| ISORALDEINE 70 | 20 |
| LEAFOVERT ® | 1 |
| LILIAL | 60 |
| LINALOOL | 60 |
| LINALYL ACETATE | 20 |
| LYRAL | 7 |
| MANZANATE | 2 |
| PHENOXANOL | 7 |
| PHENYLETHYL ALCOHOL | 120 |
| SANDAL MYSORE CORE | 2 |
| SANDRANOL ® | 7 |
| STYRALYL ACETATE | 3 |
| TAGETES RCO 10% TEC | 2 |
| TERPINEOL PURE | 20 |
| TETRAHYDROGERANIOL 10% DPG | 5 |
| TONALIDE | 7 |
| VERTOCITRAL 10% DPG | 5 |
| VERTOFIX | 15 |
| Total | 1000 |

TABLE 14

Composition of perfume oil 2 (PO2, Amounts in ‰ b.w.)

| Ingredients | Amount |
|---|---|
| Acetophenone, 10% in DPG | 10 |
| n-Undecanal | 5 |
| Aldehyde C14, so-called (peach aldehyde) | 15 |
| Allylamyl glycolate, 10% in DPG | 20 |
| Amyl salicylate | 25 |
| Benzyl acetate | 60 |
| Citronellol | 80 |
| d-Limonene | 50 |
| Decenol trans-9 | 15 |
| Dihydromyrcenol | 50 |
| Dimethylbenzylcarbinyl acetate | 30 |
| Diphenyloxide | 5 |
| Eucalyptol | 10 |
| Geraniol | 40 |
| Nerol | 20 |
| Geranium oil | 15 |
| Hexenol cis-3, 10% in DPG | 5 |
| Hexenyl salicylate cis-3 | 20 |
| Indole, 10% in DPG | 10 |
| Alpha-ionone | 15 |
| Beta-ionone | 5 |
| Lilial ® (2-methyl-3-(4-tert-butyl-phenyl)propanal) | 60 |
| Linalool | 40 |
| Methylphenyl acetate | 10 |
| Phenylethyl alcohol | 275 |
| Styrolyl acetate | 20 |
| Terpineol | 30 |
| Tetrahydrolinalool | 50 |
| Cinnamyl alcohol | 10 |
| Total: | 1000 |

TABLE 15

Composition of perfume oil 3 (PO3, Amounts in ‰ b.w.)

| Ingredients | Amount |
|---|---|
| Benzyl acetate | 60 |
| Citronellyl acetate | 60 |
| Cyclamenaldehyde (2-methyl-3-(4-isopropylphenyl)propanal | 20 |
| Dipropylene glycol (DPG) | 60 |
| Ethyllinalool | 40 |
| Florol (2-isobutyl-4-methyltetrahydro-2H-pyran-4-ol) | 30 |
| Globanone ® [(E/Z)-8-cyclohexadecen-1-one] | 180 |
| Hedione ® (methyldihydrojasmonate) | 140 |
| Hexenyl salicylate, cis-3 | 10 |
| Vertocitral (2,4-dimethyl-3-cyclohexenecarboxaldehyde) | 5 |
| Hydratropaldehyde, 10% in DPG | 5 |
| Isodamascone (1-(2,4,4-trimethyl-2-cyclohexen-1-yl)-2-buten-1-one, 10% in DPG | 5 |
| Isomuscone (cyclohexadecanone) | 40 |
| Jacinthaflor (2-methyl-4-phenyl-1,3-dioxolane) | 10 |
| Cis-jasmone, 10% in DPG | 20 |
| Linalool | 50 |
| Linalyl acetate | 30 |
| Methyl benzoate, 10% in DPG | 25 |
| para-Methyl cresol, 10% in DPG | 10 |
| Nerol | 20 |
| Phenylpropylaldehyde | 5 |
| 2-Phenylethyl alcohol | 82 |
| Tetrahydrogeraniol | 13 |
| 2,2-Dimethyl-3-cyclohexyl-1-propanol | 80 |
| Total: | 1000 |

TABLE 16

Composition of perfume oil 4 (PO4, Amounts in ‰ b.w.)

| Ingredients | Amount |
|---|---|
| AMBRETTOLIDE (MACRO) | 10 |
| AMBROXIDE 10% in IPM | 10 |
| BENZYL ACETATE | 20 |
| BENZYL SALICYLATE | 15 |
| BERGAMOT OIL. bergapten-free | 60 |
| CALONE ® 1951 10% in DPG | 15 |
| COUMARIN | 5 |
| CYCLOGALBANATE ® 10% in DPG | 10 |
| ALPHA-DAMASCONE 1% in DPG | 20 |
| DIHYDROMYRCENOL | 10 |
| ETHYL LINALOOL | 75 |
| ETHYL LINALYLACETATE | 50 |
| ETHYL MALTOL 1% in DEP | 10 |
| ETHYLENE BRASSYLATE (MACRO) | 80 |
| FLOROSA | 40 |
| GERANYLACETATE | 10 |
| HEDIONE ® HC/30 | 35 |
| HEDIONE ® | 210 |
| HELIONAL ® | 15 |
| HELVETOLIDE ® (ALICYC) | 30 |
| HEXENYLSALICYLATE CIS-3 | 20 |
| ISO E SUPER ® | 40 |
| LEAFOVERT ® 10% in DEP | 10 |
| LILIAL ® | 80 |
| LYRAL ® | 20 |
| MANDARIN OIL | 10 |
| STYRALYL ACETATE | 5 |
| SYMROSE ® | 15 |
| VANILLIN 10% in DEP | 20 |
| DIPROPYLENE GLYCOL (DPG) | 50 |
| TOTAL | 1000 |

TABLE 17

Composition of perfume oil 5 (PO5, Amounts in ‰ b.w.)

| Ingredients | Amount |
|---|---|
| AMAROCITE ® | 10 |
| AMBROCENIDE ® 10% in DPG | 5 |
| AMBROXIDE | 15 |
| AURELIONE ® (7/8-Cyclohexadecenone) (MACRO) | 70 |
| BERGAMOT OIL. bergapten-free | 90 |
| CALONE ® 1951 10% in DPG | 20 |
| CARAWAY OIL | 10 |
| CITRAL | 20 |
| COUMARIN | 10 |
| ALPHA-DAMASCONE 1% in DPG | 15 |
| DIHYDROMYRCENOL | 70 |
| ESTRAGON OIL | 10 |
| ETHYL LINALOOL | 100 |
| ETHYL LINALYLACETATE | 90 |
| EUGENOL | 10 |
| EVERNYL ® | 5 |
| FRUCTATE ® | 5 |
| GERANIUM OIL | 5 |
| HEDIONE ® HC/30 | 100 |
| HELIONAL ® | 10 |
| INDOLE 10% in DPG | 5 |
| ISO E SUPER ® | 100 |
| KEPHALIS ® | 5 |
| LAVENDER OIL | 40 |
| CITRUS OIL | 80 |
| LILIAL ® | 30 |
| MANDARIN OIL | 20 |
| MUSCENONE (MACRO) | 5 |
| SANDRANOL ® | 10 |
| VANILLIN 10% in DPG | 5 |
| DIPROPYLENE GLYCOL | 30 |
| TOTAL | 1000 |

The perfume oils PO1, PO2, PO3, PO4, or PO5 from the above examples were worked separately in each case into the formulations presented below.

Cosmetic formulations (compositions)—amounts are indicated as % by weight for all formulations.

TABLE 18

Cream o/w

| Ingredients | INCI | Amount |
|---|---|---|
| Dracorin ® CE | Glyceryl Stearate Citrate | 1.0 |
| Lanette ® O | Cetearyl Alcohol | 2.0 |
| Cutina ® GMS-V | Glyceryl Stearate | 1.0 |
| Tegosoft ® MM | Myristyl Myristate | 1.0 |
| Xiameter ® PMX-0246, Cyclosiloxane | Cyclohexasiloxane (and) Cyclopentasiloxane | 0.5 |
| Dragoxat ® 89 | Ethylhexyl Isononanoate | 2.0 |
| PCL-Liquid 100 | Cetearyl Ethylhexanoate | 4.0 |
| Neutral Oil | Caprylic/Capric Triglyceride | 4.0 |
| Carbopol ® Ultrez 21 | Acrylates/C10-30 Alkyl Acrylate Crosspolymer | 0.2 |
| Keltrol ® CG-T | Xanthan Gum | 0.1 |
| Water | Water (Aqua) | ad 100 |
| Glycerol 99, 5 P. | Glycerol | 3.0 |
| 1,2-Propylene Glycol 99 P GC | Propylene Glycol | 2.0 |
| Sodium Benzoate | Sodium Benzoate | 0.1 |
| Sodium Hydroxide 10% solution | Sodium Hydroxide | 0.5 |
| Perfume oil PO1, PO2, PO3, PO4, or PO5 | Perfume | 0.3 |
| Euxyl ® K702 | Dehydroacetic Acid, Benzoic Acid, Phenoxyethanol, Polyaminopropyl Biguanide, Ethylhexylglycerin | 0.3 |
| 3-Hydroxypropyl caprylate | Hydroxypropyl caprylate | 0.3 |
| 3-Hydroxypropyl undecylenate | Hydroxypropyl undecylenate | 0.1 |

TABLE 19

Hand and body cream

| Ingredients | INCI | Amount |
|---|---|---|
| Dracorin ® GOC | Glyceryl Oleate Citrate, Caprylic/Capric Triglyceride | 2.0 |
| PCL-Solid | Stearyl Heptanoate, Stearyl Caprylate | 2.5 |
| Lanette ® O | Cetearyl Alcohol | 1.5 |
| Cutina ® GMS-V | Glyceryl Stearate | 1.0 |
| Dragoxat ® 89 | Ethylhexyl Isononanoate | 3.0 |
| PCL-Liquid 100 | Cetearyl Ethylhexanoate | 7.0 |
| Isodragol ® | Triisononanoin | 4.0 |
| Xiameter ® PMX-0345 Cyclosiloxane | Cyclopentasiloxane (and) Cyclohexasiloxane | 0.5 |
| Water | Water (Aqua) | ad 100 |
| Carbopol ® Ultrez 21 | Acrylates/C10-30 Alkyl Acrylate Crosspolymer | 0.2 |
| Keltrol ® CG-RD | Xanthan Gum | 0.1 |
| Glycerol 85 P. | Glycerol | 3.0 |
| DragoBetaGlucan | Water (Aqua), Butylene Glycol, Glycerol, Avena Sativa (Oat) Kernel Extract | 1.5 |
| Potassium Sorbat | Potassium Sorbate | 0.1 |
| Sodium Hydroxide 10% solution | Sodium Hydroxide | 0.5 |
| Perfume oil PO1, PO2, PO3, PO4, or PO5 | Fragrance | 0.2 |
| Euxyl ® K300 | Methyl-, Butyl-, Ethyl-, Propyl, Isobutylparaben, Phenoxyethanol | 0.3 |
| 3-Hydroxypropyl caprylate | Hydroxypropyl caprylate | 0.2 |
| Glyceryl monocaprylate | Glyceryl caprylate | 0.05 |

TABLE 20

Daily face cream SPF 20

| Ingredients | Amount |
|---|---|
| SymOcide PH | 1 |
| Phenoxyethanol, Hydroxyacetophenone, Caprylyl Glycol, Water (Aqua) | |
| Ascorbyl Palmitate | 0.1 |
| Ascorbyl Palmitate | |
| Biotive L-Arginine | 0.2 |
| Arginine | |
| Buriti oil | 1 |
| *Mauritia Flexuosa* Fruit Oil | |
| Cocoa butter | 2 |
| *Theobroma Cacao* (Cocoa) Seed Butter | |
| Dimethicone | 0.5 |
| Dimethicone | |
| Disodium EDTA | 0.1 |
| Disodium EDTA | |
| Dragosantol 100 | 0.1 |
| Bisabolol | |
| Dragoxat 89 | 5 |
| Ethylhexyl Isononanoate | |
| Emulsiphos | 2 |
| Potassium Cetyl Phosphate, Hydrogenated Palm Glycerides | |
| Extrapone Corail | 1 |
| Glycerin, Aqua, Hydrolyzed Corallina Officinalis | |
| Glycerin | 3 |
| Glycerin | |
| Isoadipate | 5 |
| Diisopropyl Adipate | |
| Jojoba Wax Flakes | 1 |
| Hydrogenated Jojoba Oil | |
| Keltrol CG-T | 0.1 |
| Xanthan Gum | |
| Lanette O | 5 |
| Cetearyl Alcohol | |
| Lanette 16 | 1 |
| Cetyl Alcohol | |
| Lanette 22 | 1 |
| Behenyl Alcohol | |
| Neo Heliopan 357 | 3 |
| Butyl Methoxydibenzoylmethane | |
| Neo Heliopan HMS | 10 |
| Homosalate | |
| Neo Heliopan Hydro used as a 25% aq. Solution neutralized by arginine | 8 |
| Phenylbenzimidazole Sulfonic Acid | |
| Neo Heliopan OS | 5 |
| Ethylhexyl Salicylate | |
| Orgasol Caresse | 1 |
| Polyamide-5 | |
| Perfume oil PO1, PO2, PO3, PO4, or PO5 | 0.1 |
| Shea butter | 3 |
| *Butyrospermum Parkii* (Shea) Butter | |
| Simugel EG | 1 |
| Sodium Acrylate/Sodium Acryloyldimethyl Taurate Copolymer, Isohexadecane, Polysorbate 80 | |
| SymFinity 1298 | 0.1 |
| *Echinacea Purpurea* Extract | |
| SymMatrix | 0.1 |
| Maltodextrin, *Rubus Fructicosus* (Blackberry) Leaf Extract | |
| SymSitive 1609 | 1 |
| Pentylene Glycol, 4-t-Butylcyclohexanol | |
| Tegosoft TN | 4 |
| C12-15 Alkyl Benzoate | |
| 3-Hydroxypropyl caprylate | 0.3 |
| Glyceryl monoundecylenate | 0.1 |
| Water | ad 100 |
| Aqua | |

TABLE 21 w/o night cream

| Ingredients | INCI | Amount |
|---|---|---|
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.1 |
| Aloe Vera Gel Concentrate 10/1 * | Water (Aqua), Aloe *Barbadensis* Leaf Juice | 3.0 |
| Alugel 34 TH | Aluminium Stearate | 1.0 |
| Dragosan W/O P* | Sorbitan Isostearate, Hydrogenated Castor Oil, Ceresin, Beeswax (*Cera Alba*) | 6.0 |
| Dragosantol ® 100* | Bisabolol | 0.2 |
| Extrapone ® Witch Hazel Distillate colourless | Propylene Glycol, *Hamamelis Virginiana* (Witch Hazel) Water, (Aqua), *Hamamelis Virginiana* (Witch Hazel) Extract | 1.0 |
| Perfume oil PO1, PO2, PO3, PO4, or PO5 | Fragrance | 0.4 |
| Glycerol 85 % | Glycerin | 2.0 |
| Karion F | Sorbitol | 2.0 |
| Magnesium Chloride | Magnesium Chloride | 0.7 |
| PCL Liquid 100 | Cetearyl Ethylhexoate | 12.0 |
| Retinyl Palmitate in Oil | Retinyl Palmitate | 0.2 |
| Sun Flower Oil | *Helianthus Annuus* (Sunflower) Seed Oil | 5.0 |
| Sweet Almond Oil | *Prunus dulcis* | 5.0 |
| SymMatrix ® | Maltodextrin, *Rubus Fruticosus* (Blackberry) Leaf Extract | 1.0 |
| SymOcide PS | Phenoxyethanol, Decylene glycol, 1,2-Hexanediol | 1.0 |
| SymVital ® AgeRepair | *Zingiber Officinale* (Ginger) Root Extract | 0.1 |
| Tocopherol Acetate | Tocopheryl Acetate | 3.0 |
| Water (demineralized) | Water (Aqua) | ad 100 |

TABLE 22

Body lotion

| Ingredients | Amount |
|---|---|
| Cetearyl Alcohol | 2.0 |
| Ethylhexyl Isononanoate | 5.0 |
| Cetearyl Ethylhexanoate, Isopropyl Myristate | 3.0 |
| Glyceryl Oleate Citrate, Caprylic/Capric Triglyceride | 4.0 |
| Water (Aqua) | ad 100 |
| Carbomer | 0.3 |
| Sodium Benzoate | 0.1 |
| Propylene Glycol | 5.0 |
| Sodium Hydroxide 30% solution | 0.3 |
| Perfume oil PO1, PO2, PO3, PO4, or PO5 | 0.3 |
| Triethylene Glycol, Imidazolidinyl Urea, Methylparaben, Propylparaben, Dehydroacetic Acid | 0.3 |
| 3-Hydroxypropyl caprylate | 0.2 |
| 3-Hydroxypropyl undecylenate | 0.2 |

TABLE 23

Antibacterial body lotion, sprayable

| Ingredients | INCI | Amount |
|---|---|---|
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.05 |
| Glyceryl monoundecylenate | Glyceryl undecylenate | 0.05 |
| 2,4-Hexadienoic acid, potassium salt | Sorbic acid, potassium salt | 0.2 |
| Dow Corning 345 Fluid | Cyclomethicone | 0.5 |
| Dracorin ® GOC | Glyceryl Oleate Citrate, Caprylic/Capric Triglyceride | 2.0 |

TABLE 23-continued

Antibacterial body lotion, sprayable

| Ingredients | INCI | Amount |
|---|---|---|
| Drago-Calm | Water, Glycerin, *Avena Sativa* (Oat) Kernel Extract | 1.0 |
| Dragosantol ® 100* | Bisabolol | 0.1 |
| Perfume oil PO1, PO2, PO3, PO4, or PO5 | Fragrance | 0.3 |
| Hydrolite ®-5 | Pentylene Glycol | 5.0 |
| Neutral Oil | Caprylic/Capric Triglyceride | 4.0 |
| Paraffin Oil | Mineral Oil | 4.0 |
| PCL Liquid 100 | Cetearyl Ethylhexoate | 7.0 |
| Pemulen TR-2 | Acrylates/C10-30 Alkyl Acrylate Crosspolymer | 0.2 |
| Sodium Hydroxide (10% sol.) | Sodium Hydroxide | 0.4 |
| SymDeo ® MPP | Dimethyl Phenylbutanol | 0.5 |
| SymRelief ® 100 | Bisabolol, Zingiber Officinale (Ginger) Root Extract | 0.1 |
| Water (demineralized) | Water (Aqua) | ad 100 |

TABLE 24

Aseptic wound cream

| Ingredients | Amount |
|---|---|
| Sorbitan Isostearate, Hydrogenated Castor Oil, Ceresin, Beeswax (Cera Alba) | 6.0 |
| Petrolatum | 21.0 |
| Cera Alba | 5.0 |
| Cetearyl Alcohol | 7.0 |
| Prunus Dulcis | 7.0 |
| Lanolin | 5.0 |
| Paraffinum Liquidum | 12.0 |
| Perfume oil PO1, PO2, PO3, PO4, or PO5 | 0.3 |
| Water (Aqua) | ad 100 |
| Panthenol | 7.0 |
| Magnesium Sulfate | 0.7 |
| Pentylene Glycol | 1.0 |
| Tocopheryl Acetate | 1.0 |
| Octenidine dihydrochloride | 0.1 |
| Phenoxyethanol | 0.5 |
| 3-Hydroxypropyl caprylate | 0.4 |
| Glyceryl monocaprylate | 0.2 |

TABLE 25

Anti acne balm

| Ingredients | INCI | Amount |
|---|---|---|
| 3-Hydroxypropyl caprylate | Hydroxypropyl caprylate | 0.3 |
| 3-Hydroxypropyl undecylenate | Hydroxypropyl undecylenate | 0.2 |
| Abil 350 | Dimethicone | 1.0 |
| Allantoin | Allantoin | 0.1 |
| Aloe Vera Gel Concentrate 10/1 * | Water (Aqua), Aloe Barbadensis Leaf Juice | 3.0 |
| Azelaic Acid | Azelaic Acid | 5.0 |
| Cetiol OE | Dicaprylyl Ether | 4.0 |
| Cetiol SB 45 | Butyrospermum Parkii (Shea Butter) | 1.0 |
| D-Panthenol | Panthenol | 1.0 |
| Emulsiphos ® | Potassium Cetyl Phosphate, Hydrogenated Palm Glycerides | 2.0 |
| Perfume oil PO1, PO2, PO3, PO4, or PO5 | Fragrance | 0.2 |
| Frescolat ® ML cryst. | Menthyl Lactate | 0.8 |
| Glycerol 85% | Glycerin | 4.0 |
| Hydroviton ® PLUS | Water, Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium hyaluronate, Glucose | 1.0 |
| Lara Care A-200 | Galactoarabinan | 0.3 |
| Pemulen TR-2 | Acrylates/C10-30 Alkyl Acrylate Crosspolymer | 0.2 |
| Sodium Hydroxide (10% sol.) | Sodium Hydroxide | 0.4 |
| SymOcide PH | Hydroxyacetophenone, Phenoxyethanol, Caprylyl glycol, Aqua | 1.0 |
| Tegosoft TN | C12-15 Alkyl Benzoate | 5.0 |
| Tocopherol Acetate | Tocopheryl Acetate | 0.5 |
| Water (demineralized) | Water (Aqua) | ad 100 |

TABLE 26

Barrier repair cream

| Ingredients | INCI | Amount |
|---|---|---|
| 3-Hydroxypropyl caprylate | Hydroxypropyl caprylate | 0.1 |
| Glyceryl monocaprylate | Glyceryl caprylate | 0.1 |
| 3-Hydroxypropyl undecylenate | Hydroxypropyl undecylenate | 0.1 |
| Glyceryl nnonoundecylenate | Glyceryl undecylenate | 0.1 |
| Abil 350 | Dimethicone | 0.5 |
| Allantoin | Allantoin | 0.25 |
| Ceramide BIO* | Cetylhydroxyproline Palmitamide | 0.5 |
| Dracorin ® CE | Glyceryl Stearate Citrate | 1.5 |
| Dragoxat ® 89 | Ethylhexyl Ethylisononan-oate | 2.0 |
| Emulsiphos ® | Potassium Cetyl Phosphate, Hydrogenated Palm Glycerides | 2.0 |
| Extrapone ® Rosemary GW | Glycerin, Water (Aqua), Rosmarinus officinalis (Rosemary) Leaf Extract | 0.5 |
| Perfume oil PO1, PO2, PO3, PO4, or PO5 | Fragrance | 0.1 |
| Glycerol 85% | Glycerin | 3.0 |
| Glyceryl Stearate | Glyceryl Stearate | 2.0 |
| Hydroviton ® 24 | Water, Glycerin, Sodium Lactate, TEA Lactate, Serine, Lactic Acid, Urea, Sorbitol, Sodium Chloride, Lauryl Diethylenedi-anninoglycine, Lauryl Aminopropyl-glycine, Allantoin | 1.0 |
| Isodragol ® | Triisononanoin | 3.0 |
| Lanette O | Cetearyl Alcohol | 2.0 |
| NaOH 10% sol. | Sodium Hydroxide | 0.3 |
| Neutral Oil | Caprylic/Capric Triglyceride | 10.0 |
| SymCalmin ® | Pentylene Glycol, Butylene Glycol, Hydroxyphenyl Propamidobenzoic Acid | 1.0 |
| SymRepair ® 100 | Hexyldecanol, Bisabolol, Cetylhydroxyproline Palmitamide, Stearic Acid, Brassica Campestris (Rapeseed) Sterols | 2.0 |
| SymTriol | Caprylyl glycol, 1,2-Hexanediol, Methylbenzyl alcohol | 1.0 |
| Tegosoft PC 31 | Polyglyceryl 3-Caprate | 0.3 |
| Tocopherol Acetate | Tocopheryl Acetate | 0.3 |
| Water (demineralized) | Water (Aqua) | ad 100 |

TABLE 27

Skin soothing lotion

| Ingredients | INCI | Amount |
|---|---|---|
| 3-Hydroxypropyl caprylate | Hydroxypropyl caprylate | 0.3 |
| Glyceryl monocaprylate | Glyceryl caprylate | 0.05 |
| 3-Hydroxypropyl undecylenate | Hydroxypropyl undecylenate | 0.2 |
| Glyceryl monoundecylenate | Glyceryl undecylenate | 0.05 |
| Abil 350 | Dimethicone | 2.0 |
| Allantoin | Allantoin | 0.2 |
| Carbopol Ultrez-10 | Carbomer | 0.1 |
| Ceramide BIO* | Cetylhydroxyproline Palmitamide | 0.1 |
| Citric Acid 10% sol. | Citric Acid | 0.4 |
| Emulsiphos ® | Potassium Cetyl Phosphate, Hydrogenated Palm Glycerides | 2.0 |
| Extrapone ® Green Tea GW | Glycerin, Water (Aqua), Camellia Sinensis Leaf Extract | 0.2 |
| Extrapone ® Rosemary GW | Glycerin, Water (Aqua), Rosmarinus officinalis (Rosemary) Leaf Extract | 0.3 |
| Perfume oil PO1, PO2, PO3, PO4, or PO5 | Fragrance | 0.3 |
| Glycerol 85% | Glycerin | 2.0 |
| Glyceryl Stearate | Glyceryl Stearate | 2.0 |
| Isodragol ® | Triisononanoin | 2.0 |
| Keltrol RD | Xanthan Gum | 0.1 |
| Lanette O | Cetearyl Alcohol | 3.0 |
| Neo PCL wssl. N | Trideceth-9, PEG-5 Ethylhexanoate, Water | 1.0 |
| PCL Liquid 100 | Cetearyl Ethylhexanoate | 5.0 |
| PCL Solid | Stearyl Heptanoate, Stearyl Caprylate | 2.0 |
| Propylene Glycol | Propylene Glycol | 5.0 |
| Sodium Hydroxide (10% sol.) | Sodium Hydroxide | 0.3 |
| SymCalmin ® | Pentylene Glycol, Butylene Glycol, Hydroxyphenyl Propamidobenzoic Acid | 2.0 |
| SymMatrix ® | Maltodextrin, Rubus Fruticosus (Blackberry) Leaf Extract | 0.1 |
| SymSave H | Hydroxyacetophenone | 0.4 |
| 2-Phenoxyethyl Alcohol | Phenoxyethanol | 0.4 |
| SymSitive ® 1609 | Pentylene Glycol, 4-t-Butylcyclohexanol | 1.5 |
| Water (demineralized) | Water (Aqua) | ad 100 |

TABLE 28

Baby Nappy Rash Cream w/o

| Ingredients | Amount |
|---|---|
| SymOcide PH | |
| Phenoxyethanol, Hydroxyacetophenone, Caprylyl Glycol, Water (Aqua) | 1 |
| Cupuaçu butter | |
| Theobroma Grandiflorum Seed Butter | 1 |
| Cutina HR Powder | |
| Hydrogenated Castor Oil | 1.5 |
| Dehymuls PGPH | |
| Polyglyceryl-2 Dipolyhydroxystearate | 5 |

TABLE 28-continued

Baby Nappy Rash Cream w/o

| Ingredients | Amount |
|---|---|
| Glycerin | |
| Glycerin | 5 |
| Jojoba oil | |
| Simmondsia Chinensis (Jojoba) Seed Oil | 5 |
| Magnesium Sulfate Hepta Hydrate | |
| Magnesium Sulfate | 0.5 |
| Monomuls 90-O18 | |
| Glyceryl Oleate | 1 |
| Neutral oil | |
| Caprylic/capric triglyceride | 8 |
| PCL Liquid 100 | |
| Cetearyl Ethylhexanoate | 5 |
| SymCalmin | |
| Butylene Glycol, Pentylene Glycol, Hydroxyphenyl Propamidobenzoic Acid | 1 |
| Tamanu oil | |
| Calophyllum Inophyllum Seed Oil | 0.2 |
| Tetrasodium EDTA | |
| Tetrasodium EDTA | 0.1 |
| Titan dioxide | |
| Titan dioxide | 4 |
| Water | |
| Aqua | ad 100 |
| Wheat germ oil | |
| Triticum Vulgare (Wheat) Germ Oil | 2 |
| Zinc oxide | |
| Zinc oxide | 10 |
| 3-Hydroxypropyl caprylate | 0.3 |
| 3-Hydroxypropyl undecylenate | 0.15 |

TABLE 29

Skin lightening day cream o/w

| Ingredients | INCI | Amount |
|---|---|---|
| 3-Hydroxypropyl caprylate | Hydroxypropyl caprylate | 0.1 |
| Glyceryl monocaprylate | Glyceryl caprylate | 0.1 |
| 3-Hydroxypropyl undecylenate | Hydroxypropyl undecylenate | 0.05 |
| Glyceryl monoundecylenate | Glyceryl undecylenate | 0.05 |
| Abil 350 | Dimethicone | 0.5 |
| Dracorin ® CE | Glyceryl Stearate Citrate | 2.5 |
| Dracorin ® GOC | Glyceryl Oleate Citrate, Caprylic/Capric Triglyceride | 0.5 |
| Drago-Beta-Glucan | Water (Aqua), Butylene Glycol, Glycerin, Avena Sativa (Oat), Kernel Extract | 0.3 |
| Dragosantol ® 100* | Bisabolol | 0.2 |
| Perfume oil PO1, PO2, PO3, PO4, or PO5 | Fragrance | 0.1 |
| Frescolat ® MGA | Menthone Glycerol Acetal | 0.5 |
| Glycerol 85% | Glycerin | 3.0 |
| Isopropyl Palmitate | Isopropyl Palmitate | 4.0 |

TABLE 29-continued

Skin lightening day cream o/w

| Ingredients | INCI | Amount |
|---|---|---|
| Keltrol RD | Xanthan Gum | 0.2 |
| Lanette 16 | Cetyl Alcohol | 1.0 |
| Neo Heliopan ® AV | Ethylhexyl Methoxy-cinnamate | 5.0 |
| Neutral Oil | Caprylic/Capric Triglyceride | 6.0 |
| PCL Liquid 100 | Cetearyl Ethylhexoate | 3.0 |
| Sodium Benzoate | Sodium Benzoate | 0.1 |
| Symdiol ® 68T | 1,2-Hexanediol, Caprylylglycol, Tropolone | 0.5 |
| SymVital ® AgeRepair | Zingiber Officinale (Ginger) Root Extract | 0.1 |
| SymWhite ® 377 | Phenylethyl Resorcinol | 0.5 |
| Water (demineralized) | Water (Aqua) | ad 100 |

TABLE 30

Shampoo

| Ingredients | Amount |
|---|---|
| 4-Hydroxyacetophenone (SymSave H) | |
| Hydroxyacetophenone Antil 127 | 0.3 |
| PEG-120 Methyl Glucose Dioleate Brazilian nut oil | 0.5 |
| Bertholletia Excelsa Seed Oil Cocamidopropyl Betaine 38% | 0.5 |
| Cocamidopropyl Betaine Octopirox | 5 |
| Piroctone olamine Dragoderm | 0.3 |
| Glycerin, Triticunn Vulgare Gluten, Aqua Fragrance | 0.5 |
| Perfum Glycerin | 0.5 |
| Glycerin Jojoba oil | 0.5 |
| Simmondsia Chinensis (Jojoba) Seed Oil Marlinat 242/90 M | 0.5 |
| MIPA Laureth Sulfate, Propylene Glycol Marlowet CG | 15 |
| PEG-18 Castor Oil Dioleate Plantacare 1200 UP | 2 |
| Lauryl Glucoside Polyquaternium-10 | 0.5 |
| Polyquaternium-10 Sodium Chloride | 0.3 |
| Sodium Chloride SymCalmin | 1.5 |
| Butylene Glycol, Pentylene Glycol, Hydroxyphenyl Propamidobenzoic Acid | 1 |

TABLE 30-continued

Shampoo

| Ingredients | Amount |
|---|---|
| SymOcide PS | |
| Phenoxyethanol, Decylene Glycol, 1,2-Hexanediol | 0.8 |
| 3-Hydroxypropyl caprylate | 0.4 |
| 3-Hydroxypropyl undecylenate | 0.2 |
| Water | |
| Aqua | ad 100 |

TABLE 31

Anti dandruff shampoo

| Ingredients | INCI | Amount |
|---|---|---|
| 3-Hydroxypropyl caprylate | Hydroxypropyl caprylate | 0.3 |
| Glyceryl monocaprylate | Glyceryl caprylate | 0.2 |
| 3-Hydroxypropyl undecylenate | Hydroxypropyl undecylenate | 0.15 |
| Aloe Vera Gel Concentrate 10/1 * | Water (Aqua), Aloe Barbadensis Leaf Juice | 0.5 |
| Avocado oil | Persea Gratissima (Avocado) Oil | 0.5 |
| Citric Acid 10% sol. | Citric Acid | 0.3 |
| Comperlan 100 | Cocamide MEA | 0.5 |
| Crinipan AD | Climbazole | 0.2 |
| Dragoderm ® | Glycerin, Triticum Vulgare (Wheat) Gluten, Water (Aqua) | 2.0 |
| Perfume oil PO1, PO2, PO3, PO4, or PO5 | Fragrance | 0.5 |
| Genapol LRO liquid | Sodium Laureth Sulfate | 37.0 |
| Merquat 550 | Polyquaternium-7 | 0.5 |
| Sodium Chloride | Sodium Chloride | 1.0 |
| SymSave ® H | Hydroxyacetophenone | 0.8 |
| Tego Betain L7 | Cocamidopropyl Betaine | 6.0 |
| Water (demineralized) | Water (Aqua) | ad 100 |

TABLE 32

2-in-1 Shampoo

| Ingredients | INCI Name | Amount |
|---|---|---|
| Deionized water | Water | ad 100 |
| Shea butter | Butyrospermum Parkii (Shea) Butter | 0.1 |
| Plantacare PS 10 | Sodium Laureth Sulfate, Lauryl Glucoside | 20.0 |
| Euperlan PK 771 | Glycol Distearate, Sodium Lauryl Sulfate, Cocamide MEA, Laureth-10 | 6.0 |
| Sodium chloride | Sodium Chloride | 1.4 |
| Citric acid monohydrate crystalline | Citric acid | 0.1 |
| Perfume oil PO1, PO2, PO3, PO4, or PO5 | Fragrance | 0.5 |
| Phenoxyethanol, Methylparaben, Ethylparaben | Phenoxyethanol, Methylparaben, Ethylparaben | 0.5 |

TABLE 32-continued

2-in-1 Shampoo

| Ingredients | INCI Name | Amount |
|---|---|---|
| Zinc Omadine | Zinc pyrithione | 0.10 |
| 3-Hydroxypropyl caprylate | Hydroxypropyl caprylate | 0.3 |
| 3-Hydroxypropyl undecylenate | Hydroxypropyl undecylenate | 0.15 |

TABLE 33

Body wash

| Ingredients | INCI | Amount |
|---|---|---|
| Lumerol K 28 | Disodium Laureth Sulfosuccinate, Cocamidopropyl Betaine, Magnesium Lauryl Sulfate | 33.0 |
| Amphotensid B 4 | Cocamidopropyl Betaine | 10.0 |
| Perlglanzmittel GM 4055 | MIPA-Pareth-25 Sulfate, Glycol Stearate | 4.0 |
| Sodium Chloride | Sodium Chloride | 2.0 |
| Avocado oil | Persea Gratissima (Avocado) Oil | 3.0 |
| SymSave H | Hydroxyacetophenone | 0.8 |
| Water | Water | ad 100 |
| Perfume oil PO1, PO2, PO3, PO4, or PO5 | Fragrance | 0.5 |
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.1 |
| Glyceryl monoundecylenate | Glyceryl undecylenate | 0.1 |

TABLE 34

Shower gel

| Ingredients | INCI | Amount |
|---|---|---|
| Deionized water | Water | ad 100 |
| Shea butter | Butyrospermum Parkii (Shea) Butter | 1.0 |
| Plantacare PS 10 | Sodium Laureth Sulfate, Lauryl Glucoside | 20.0 |
| Dehydroacetic acid | Dehydroacetic acid | 0.2 |
| SymSave H | Hydroxyacetophenone | 0.3 |
| Sodium chloride | Sodium Chloride | 1.4 |
| Citric acid monohydrate crystalline | Citric Acid | 1.3 |
| Perfume oil PO1, PO2, PO3, PO4, or PO5 | Fragrance | 0.6 |
| 3-Hydroxypropyl caprylate | Hydroxypropyl caprylate | 0.1 |
| Glyceryl monocaprylate | Glyceryl caprylate | 0.3 |
| 3-Hydroxypropyl undecylenate | Hydroxypropyl undecylenate | 0.2 |

TABLE 35

Intimate wash

| Ingredients | INCI | Amount |
|---|---|---|
| Tegobetaine HS | Cocamidopropyl Betaine, Glyceryl Laurate | 15.0 |
| Tagat L 2 | PEG-20 Glyceryl Laurate | 2.0 |

TABLE 35-continued

Intimate wash

| Ingredients | INCI | Amount |
|---|---|---|
| Arlacide G | Chlorhexidine Digluconate | 0.1 |
| Rewoquat B 50 | Benzalkonium Chloride | 0.1 |
| Lactic Acid, 80% | Lactic Acid | 0.1 |
| euxyl ® K700 | Potassium Sorbate, Benzyl Alcohol, Phenoxyethanol | 0.3 |
| Water | Water | ad 100 |
| Perfume oil PO1, PO2, PO3, PO4, or PO5 | Fragrance | 0.2 |
| 3-Hydroxypropyl caprylate | Hydroxypropyl caprylate | 0.3 |
| Glyceryl monocaprylate | Glyceryl caprylate | 0.1 |
| 3-Hydroxypropyl undecylenate | Hydroxypropyl undecylenate | 0.1 |
| Glyceryl monoundecylenate | Glyceryl undecylenate | 0.05 |

TABLE 36

Liquid soap, transparent

| Ingredients | INCI | Amount |
|---|---|---|
| Tagat O 2 | PEG-20 Glyceryl Oleate | 2.5 |
| Coconut oil diethanolamine condensate | Cocamide DEA | 5.0 |
| Abil B 8842 | Cyclomethicone | 0.5 |
| Sodium laurylethersulfate, 28% | Sodium Laureth Sulfate | 35.0 |
| Tego-Betaine L7 | Cocamidopropyl Betaine | 5.0 |
| Soap, 25% | Coconut acid, Potassium salt, Potassium Oleate | 20.0 |
| Perfume oil PO1, PO2, PO3, PO4, or PO5 | Fragrance | 0.4 |
| Preservative | DMDM Hydantoin | 0.2 |
| 3-Hydroxypropyl caprylate | Hydroxypropyl caprylate | 0.15 |
| Glyceryl monocaprylate | Glyceryl caprylate | 0.15 |
| Water | Water | ad 100 |

TABLE 37

Syndet soap, liquid

| Ingredients | INCI | Amount |
|---|---|---|
| Elfan OS 46 | Sodium Olefin C14-C16 Sulfonate | 35.5 |
| Armoteric LB | Lauryl Betaine | 8.0 |
| Euperlan PK 3000 OK | Glycol Distearate, Glycerin, Laureth-4, Cocamidopropyl Betaine | 10.0 |
| Elfacos GT 282 L | Talloweth-60 Myristyl Glycol | 3.0 |
| PCL-Liquid 100 | Cetearyl Ethylhexanoate | 4.0 |
| Perfume oil PO1, PO2, PO3, PO4, or PO5 | Fragrance | 0.4 |
| SymSave H | 4-Hydroxyacetophenone | 0.6 |
| 3-Hydroxypropyl caprylate | Hydroxypropyl caprylate | 0.15 |
| 3-Hydroxypropyl undecylenate | Hydroxypropyl undecylenate | 0.25 |
| Water | Water | ad 100 |

TABLE 38

Anti-acne wash

| Ingredients | Amount |
| --- | --- |
| Water (Aqua) | ad 100 |
| Polyquaternium-7 | 0.5 |
| Cocamidopropyl Betaine | 9.0 |
| Coco Glucoside | 2.0 |
| Polysorbate 80, Glycerol, Gossypium Herbaceum, (Cotton) Seed Oil, Water (Aqua) | 1.0 |
| Trideceth-9, PEG-5 Ethylhexanoate, Water (Aqua) | 1.0 |
| Glycereth-90 Isostearate, Laureth-2 | 0.5 |
| Sodium Laureth Sulfate | 37.0 |
| Glycerol, Triticum Vulgare (Wheat) Gluten, Water (Aqua) | 1.0 |
| Sodium Chloride | 0.3 |
| Perfume oil PO1, PO2, PO3, PO4, or PO5 | 1.0 |
| SymOcide BHO (Hydroxyacetophenone, Benzyl alcohol, Caprylyl glycol, Water) | 1.0 |
| 3-Hydroxypropyl caprylate | 0.25 |
| 3-Hydroxypropyl undecylenate | 0.15 |

TABLE 39

Mineral wash and cleaning gel

| Ingredients | INCI | Amount |
| --- | --- | --- |
| Water | Water (Aqua) | ad 100 |
| Pionier ® NP 37 G | Sodium Carbomer | 1.5 |
| SymSol ® PF-3 | Water (Aqua), Pentylene Glycol, Sodium Lauryl Sulfoacetate, Sodium Oleoyl Sarcosinate, Sodium Chloride, Disodium Sulfoacetate, Sodium Oleate, Sodium Sulfate | 5.0 |
| Hydroviton ® 24 | Water (Aqua), Pentylene Glycol, Glycerol, Sodium Lactate, Lactic Acid, Serine, Urea, Sorbitol, Sodium Chloride, Allantoin | 1.0 |
| Extrapone ® Silk GW | Water (Aqua), Glycerol, Hydrolyzed Silk | 1.0 |
| Hydrolite ® 5 | Pentylene Glycol | 4.0 |
| Actipearls Red Star # DH10402/6 | Water (Aqua), Propylene Glycol, Algin, Gellan Gum, Xanthan Gum, CalciumChloride, CI 12490 (Pigment Red 5), Mica (CI 77019), Titanium Dioxide (CI 77891) | 1.0 |
| Perfume oil PO1, PO2, PO3, PO4, or PO5 | Fragrance | 0.5 |
| SymGuard CD | Phenylpropanol, o-cymen-5-ol, Decylene glycol | 0.3 |
| 3-Hydroxypropyl caprylate | Hydroxypropyl caprylate | 0.2 |
| 3-Hydroxypropyl undecylenate | Hydroxypropyl undecylenate | 0.1 |

TABLE 40

After Shave Tonic

| Ingredients | INCI | Amount |
| --- | --- | --- |
| SymSol ® PF-3 | Water (Aqua), Pentylene Glycol, Sodium Lauryl Sulfoacetate, Sodium Oleoyl Sarcosinate, Sodium Chloride, Disodium Sulfoacetate, SodiumOleate, Sodium Sulfate | 3.0 |
| SymSitive ® 1609 | Pentylene Glycol, 4-t-Butylcyclohexanol | 1.0 |
| Frescolat ® ML | Menthyl Lactate | 0.3 |
| Glycerol 99,5 P. | Glycerol | 5.0 |
| Water | Water (Aqua) | ad 100 |
| Extrapone ® Glacier Water GW | Glycerol, Water (Aqua) | 1.0 |
| SymCalmin ® | Butylene Glycol, Pentylene Glycol, Hydroxyphenyl Propamidobenzoic Acid | 0.5 |
| Dragosine ® | Carnosine | 0.1 |
| Hydrolite ® 5 | Pentylene Glycol | 5.0 |
| Ethanol 96% | Alcohol Denat. | 5.0 |
| Colour Pigment | Colour Pigment | 0.05 |
| Perfume oil PO1, PO2, PO3, PO4, or PO5 | Fragrance | 0.15 |
| 3-Hydroxypropyl caprylate | Hydroxypropyl caprylate | 0.1 |
| 3-Hydroxypropyl undecylenate | Hydroxypropyl undecylenate | 0.05 |

TABLE 41

Hair conditioner with Crinipan, rinse-off

| Ingredients | INCI | Amount |
| --- | --- | --- |
| Lanette ® O | Cetearyl Alcohol | 4.0 |
| Dragoxat 89 | Ethylhexyl Isononanoate | 2.0 |
| Genamin ® KDM-P | Behentrimonium Chloride | 1.0 |
| SF 1550 | Phenyl Trimethicone | 0.1 |
| Neo Heliopan ® BB | Benzophenone-3 | 0.1 |
| Crinipan ® AD | Climbazole | 0.4 |
| Glycerol 99,5 P. | Glycerol | 6.0 |
| Water | Water (Aqua) | ad 100 |
| Actipone ® Alpha Pulp | Water (Aqua), Butylene Glycol, Malic Acid, Actinidia Chinensis (Kiwi) Fruit Juice, Citrus Aurantium Dulcis (Orange) Juice, Citrus Paradisi (Grapefruit) Juice, Pyrus Malus (Apple) Juice, Trideceth-9, Prunus Amygdalus Dulcis (Sweet Almond) Seed Extract | 0.5 |
| Extrapone ® Bamboo P | Propylene Glycol, Water (Aqua), Butylene Glycol, Bambusa Vulgaris Shoot Extract | 0.5 |
| Sodium Hydroxide 10% solution | Sodium Hydroxide | 0.4 |
| Colour I | Colour | 0.6 |
| Colour II | Colour | 0.3 |
| Perfume oil PO1, PO2, PO3, PO4, or PO5 | Fragrance | 0.4 |
| Preservative | Methylparaben | 0.3 |
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.15 |

TABLE 42

Scalp soothing hair conditioner with UV-B/UV-A protection, rinse off

| Ingredients | INCI | Amount |
| --- | --- | --- |
| 3-Hydroxypropyl caprylate | Hydroxypropyl caprylate | 0.2 |
| Glyceryl monocaprylate | Glyceryl caprylate | 0.2 |
| 3-Hydroxypropyl undecylenate | Hydroxypropyl undecylenate | 0.1 |
| Glyceryl monoundecylenate | Glyceryl undecylenate | 0.1 |
| Abil 350 | Dimethicone | 0.1 |
| Dehyquart A CA | Cetrimonium Chloride | 0.5 |
| Dehyquart SP | Quaternium-52 | 4.0 |

TABLE 42-continued

Scalp soothing hair conditioner with UV-B/UV-A protection, rinse off

| Ingredients | INCI | Amount |
|---|---|---|
| Dracorin ® CE | Glyceryl Stearate Citrate | 1.0 |
| EDETA BD | Disodium EDTA | 0.1 |
| Extrapone ® Green Tea GW | Glycerin, Water (Aqua), Camellia Sinensis Leaf Extract | 0.7 |
| Perfume oil PO1, PO2, PO3, PO4, or PO5 | Fragrance | 0.5 |
| Lara Care A-200 | Galactoarabinan | 0.5 |
| Neutral Oil | Caprylic/Capric Triglyceride | 1.0 |
| PCL Liquid 100 | Cetearyl Ethylhexoate | 0.3 |
| PCL Solid | Stearyl Heptanoate, Stearyl Caprylate | 3.0 |
| SymOcide ®PS | Phenoxyethanol, Decylene Glycol, 1,2-Hexanediol | 1.0 |
| Water (demineralized) | Water (Aqua) | ad 100 |

TABLE 43

Hair conditioner with UV protection

| Ingredients | INCI | Amount |
|---|---|---|
| Renex PEG 6000 | PEG-150 | 2.5 |
| Hair Conditioner Base | Cetyl alcohol, behentrimonium chloride, Triticum Vulgare (Wheat) bran extract, linoleic acid | 3.0 |
| PCL-Solid | Stearyl heptanoate, stearyl caprylate | 0.5 |
| Dow Corning 5200 | Laurylmethicone copolyol | 0.5 |
| Natrosol 250 HR | Hydroxyethylcellulose | 0.5 |
| Benzophenone-4 | Benzophenone-4 | 1.0 |
| Neo Heliopan AP | Disodiumphenyldibenz-imidazole tetrasulphonate | 1.0 |
| Amino methyl propanol | Amino methyl propanol | 2.0 |
| Dow Corning 949 cationic emulsion | Amodimethicone, cetrimonium chloride, trideceth-12 | 2.0 |
| Perfume oil PO1, PO2, PO3, PO4, or PO5 | Fragrance | 0.8 |
| 1,2-Hexanediol | 1,2-Hexanediol | 0.5 |
| 3-Hydroxypropyl caprylate | Hydroxypropyl caprylate | 0.2 |
| 3-Hydroxypropyl undecylenate | Hydroxypropyl undecylenate | 0.1 |
| Water | Water (Aqua) | ad 100 |

TABLE 44

Hair conditioner, leave on

| Ingredients | INCI | Amount |
|---|---|---|
| 3-Hydroxypropyl caprylate | Hydroxypropyl caprylate | 0.15 |
| Glyceryl monocaprylate | Glyceryl caprylate | 0.2 |
| 3-Hydroxypropyl undecylenate | Hydroxypropyl undecylenate | 0.1 |
| Glyceryl monoundecylenate | Glyceryl undecylenate | 0.05 |
| Dehyquart A CA | Cetrimonium Chloride | 0.2 |
| Dehyquart SP | Quaternium-52 | 2.0 |
| Dracorin ® CE | Glyceryl Stearate Citrate | 1.0 |
| Drago-Calm | Water, Glycerin, Avena Sativa (Oat) Kernel Extract | 2.0 |
| Farnesol | Farnesol | |
| Perfume oil PO1, PO2, PO3, PO4, or PO5 | Fragrance | 0.5 |
| Lara Care A-200 | Galactoarabinan | 0.1 |
| Polymer JR 400 | Polyquaternium-10 | 0.1 |
| Propylene Glycol | Propylene Glycol | 0.8 |
| SymMollient ® WS | Trideceth-9, PEG-5 Isononanoate, Water | 1.0 |
| SymSol ®PF3* | Water, Pentylene Glycol, Sodium Lauryl Sulfoacetate, Sodium Oleoyl Sarcosinate, Sodium Chloride, Disodium Sulfoacetate, Sodium Oleate, Sodium Sulfate | 1.5 |

TABLE 44-continued

Hair conditioner, leave on

| Ingredients | INCI | Amount |
|---|---|---|
| SymTriol ® | Caprylyl Glycol, 1,2-Hexanediol, Methylbenzyl Alcohol | 1.0 |
| Water (demineralized) | Water (Aqua) | ad 100 |

TABLE 45

Anti-itch hair conditioner, leave on

| Ingredients | INCI | Amount |
|---|---|---|
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.1 |
| (-)-alpha Bisabolol | Bisabolol | 0.1 |
| Dehyquart A CA | Cetrimonium Chloride | 0.5 |
| Dehyquart SP | Quaternium-52 | 4.0 |
| Dracorin ® CE* | Glyceryl Stearate Citrate | 1.0 |
| Drago-Oat-Active* | Water (Aqua), Butylene Glycol, Avena Sativa (Oat) Kernel Extract | 2.0 |
| Perfume oil PO1, PO2, PO3, PO4, or PO5 | Fragrance | 0.1 |
| Lara Care A-200 | Galactoarabinan | 1.5 |
| Neutral Oil | Caprylic/Capric Triglyceride | 1.0 |
| PCL Liquid 100* | Cetearyl Ethylhexoate | 0.3 |
| Polymer JR 400 | Polyquaternium-10 | 0.1 |
| Propylene Glycol | Propylene Glycol | 0.8 |
| SymGlucan ® | Aqua, Glycerin, 1,2-Hexandiol, Caprylyl Glycol, Beta-Glucan | 5 |
| SymMollient ® W/S | Trideceth-9, PEG-5 Isononanoate, Water (Aqua) | 2.0 |
| SymOcide ® PH | Phenoxyethanol, Hydroxyacetophenone, Caprylyl Glycol, Aqua | 1.2 |
| SymSol ®PF3 * | Water, Pentylene Glycol, Sodium Lauryl Sulfoacetate, Sodium Oleoyl Sarcosinate, Sodium Chloride, Disodium Sulfoacetate, Sodium Oleate, Sodium Sulfate | 1.5 |
| Water, demineralized | Water (Aqua) | ad 100 |

TABLE 46

Sprayable hair conditioner with zinc pyrithrione, leave-on

| Ingredients | INCI | Amount |
|---|---|---|
| Monomuls 60-35 C | Hydrogenated Palm Glycerides | 1.7 |
| Cetiol OE | Dicaprylyl Ether | 7.2 |
| Abil 100 | Dimethicone | 3.6 |
| Dehyquart F 75 | Distearoylethyl Hydroxyethylmonium, Methosulfate, Cetearyl Alcohol | 4.0 |
| Eumulgin B1 | Ceteareth-12 | 3.5 |
| Cetiol S | Diethylhexylcyclohexane | 7.2 |
| D-Panthenol | Panthenol | 0.1 |
| Glycerol 99,5 P. | Glycerol | 1.5 |
| Water | Water (Aqua) | ad 100 |
| Actipone ® Rosemary | Water (Aqua), Propylene, Glycol, Rosmarinus Officinalis, (Rosemary) Leaf Extract | 0.1 |
| Frescolat ® ML Cryst. | Menthyl Lactate | 0.5 |
| Dragosantol100 | Bisabolol | 0.1 |
| Zinc Omadine | Zinc pyrithione | 0.1 |
| Perfume oil PO1, PO2, PO3, PO4, or PO5 | Fragrance | 0.4 |

TABLE 46-continued

Sprayable hair conditioner with zinc pyrithrione, leave-on

| Ingredients | INCI | Amount |
|---|---|---|
| 2-Phenoxyethyl alcohol | Phenoxyethanol | 0.4 |
| SymSave H | Hydroxyacetophenone | 0.3 |
| SymDiol 68 | 1,2-Hexanediol, Caprylyl glycol | 0.3 |
| 3-Hydroxypropyl caprylate | Hydroxypropyl caprylate | 0.4 |
| 3-Hydroxypropyl undecylenate | Hydroxypropyl undecylenate | 0.1 |

TABLE 47

Hair styling gel

| Ingredients | Amount |
|---|---|
| Water | ad 100 |
| PVM/MA Decadiene Crosspolymer | 0.6 |
| PVP | 3.0 |
| Isocetyl Stearate | 4.0 |
| Ethylhexyl Methoxycinnamate | 0.5 |
| Aminomethyl Propanol | 0.4 |
| Perfume oil PO1, PO2, PO3, PO4, or PO5 | 0.6 |
| SymDiol ® 68T (1,2-Hexanediol, 1,2-Octanediol, Tropolone) | 0.4 |
| Phenoxyethanol | 0.3 |
| 3-Hydroxypropyl caprylate | 0.2 |
| 3-Hydroxypropyl undecylenate | 0.1 |

TABLE 48

Deodorant stick

| Ingredients | Amount |
|---|---|
| Sodium stearate | 8.0 |
| PPG-3 Myristyl ether | 70.0 |
| 1,2-propylene glycol | 10.0 |
| 1,1-dimethyl-3-phenylpropanol | 0.2 |
| 2-butyloctanoic acid | 0.2 |
| Perfume oil PO1, PO2, PO3, PO4, or PO5 | 0.6 |
| Water | ad 100 |
| SymDeo Plus (Jasmol (2-benzlheptanol), 1-Dodecanol (Lauryl Alcohol), 1,2-Decanediol (Decylene Glycol), 2-Phenoxyethyl Alcohol (Phenoxyethanol)) | 0.5 |
| 3-Hydroxypropyl caprylate | 0.15 |
| Glyceryl monocaprylate | 0.15 |
| 3-Hydroxypropyl undecylenate | 0.1 |

TABLE 49

Zirconium suspensoid antiperspirant stick

| Ingredients | INCI | Amount |
|---|---|---|
| PCL Liquid 100 | Cetearyl ethylhexanonate | ad 100 |
| Silicone Fluid 345 | Cyclomethicone | 10.0 |
| CRODACOL C90 | Cetyl Alcohol | 8.0 |
| SYNCROWAX HGLC | C18-36 Triglyceride | 8.0 |
| CRODAMOL PTC | Pentaerythritol Tetracaprylate/Caprate | 5.0 |
| SYNCROWAX HRC | Tribehenin | 4.0 |
| VOLPO N5 | Oleth-5 | 1.0 |
| Titanium Dioxide | | 1.0 |
| Rezal 36GP | Aluminium Tetrachlorohydrex GLY | 20.0 |
| Dry Flo C | Aluminium Starch Octenyl Succinate | 22.5 |
| Preservative | Phenoxyethanol | 0.8 |
| Perfume oil PO1, PO2, PO3, PO4, or PO5 | Fragrance | 0.6 |

TABLE 49-continued

Zirconium suspensoid antiperspirant stick

| Ingredients | INCI | Amount |
|---|---|---|
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.1 |
| Glyceryl monoundecylenate | Glyceryl undecylenate | 0.1 |

TABLE 50

Antiperspirant/deodorant roll-on

| Ingredients | INCI | Amount |
|---|---|---|
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.1 |
| Dragosantol ® 100* | Bisabolol | 0.1 |
| Ethanol 96% | Ethanol | 30.0 |
| Farnesol | Farnesol | 0.5 |
| Perfume oil PO1, PO2, PO3, PO4, or PO5 | Fragrance | 1.5 |
| Frescolat ®ML cryst. | Menthyl Lactate | 0.2 |
| Irgasan DP 300 | Triclosan | 0.3 |
| Natrosol 250 HHR | Hydroxyethyl-cellulose | 0.3 |
| Solubilizer 611674 | PEG-40 Hydrogenated Castor Oil, Trideceth-9, Water (Aqua) | 2.0 |
| SymDeo ® B125 | 2-Methyl 5-Cyclohexylpentanol | 0.5 |
| Water (demineralized) | Water (Aqua) | ad 100 |
| Zirkonal L 450 | Aluminium Zirconium Pentachlorohydrate (40% aqueous solution) | 37.0 |

TABLE 51

Deodorant formulation in the form of a roll-on gel

| Ingredients | Amount |
|---|---|
| 1,3-butylene glycol | 2.0 |
| PEG-40-hydrogenated castor oil | 2.0 |
| Hydroxyethylcellulose | 0.5 |
| Perfume oil PO1, PO2, PO3, PO4, or PO5 | 0.3 |
| 1,3-propanediol | 0.5 |
| SymGuard CD (3-Phenylpropanol, o-cymen-3-ol, Decylene glycol) | 0.4 |
| Ethylhexyl glycerin | 0.1 |
| 3-Hydroxypropyl caprylate | 0.3 |
| Glyceryl monocaprylate | 0.15 |
| 3-Hydroxypropyl undecylenate | 0.1 |
| Water | ad 100 |

TABLE 52

Clear deo anti-perspirant roll-on

| Ingredients | INCI | Amount |
|---|---|---|
| Methocel E4M Premium | Hydroxypropyl Methylcellulose | 0.5 |
| Water | Water (Aqua) | ad 100 |
| Neo-PCL Water Soluble N | Trideceth-9, PEG-5 Ethylhexanoate, Water (Aqua) | 1.0 |
| Solubilizer | PEG-40 Hydrogenated Castor Oil, Trideceth-9, Propylene Glycol, Water (Aqua) | 3.0 |

TABLE 52-continued

Clear deo anti-perspirant roll-on

| Ingredients | INCI | Amount |
|---|---|---|
| Deolite | Dimethyl Phenylpropanol, Pentylene Glycol | 0.5 |
| Locron LW | Aluminium Chlorohydrate | 25.0 |
| Aloe Vera Gel Concentrate 10/1 | Aloe Barbadensis Leaf Juice | 1.0 |
| 1,2-Propylene Glycol 99 P GC | Propylene Glycol | 4.0 |
| Ethanol 96% | Alcohol Denat. | 30.0 |
| Perfume oil PO1, PO2, PO3, PO4, or PO5 | Fragrance | 1.0 |
| 3-Hydroxypropyl caprylate | Hydroxypropyl caprylate | 0.3 |
| 3-Hydroxypropyl undecylenate | Hydroxypropyl undecylenate | 0.15 |

TABLE 53

Deodorant pump spray with SymClariol

| Ingredients | INCI | Amount |
|---|---|---|
| SymClariol ® | Decylene Glycol | 0.2 |
| Solubilizer | PEG-40 Hydrogenated Castor Oil, Trideceth-9, Propylene Glycol, Water (Aqua) | 4.0 |
| Neo-PCL Water Soluble N | Trideceth-9, PEG-5 Ethylhexanoate, Aqua | 1.5 |
| SymRelief ® | Bisabolol, Zingiber Officinale (Ginger) Root Extract | 0.1 |
| Water | Water (Aqua) | ad 100 |
| 1,2-Propylene Glycol | Propylene Glycol | 6.0 |
| Perfume oil PO1, PO2, PO3, PO4, or PO5 | Perfume | 0.4 |
| SymDiol ® 68 | 1,2-Hexanediol, Caprylyl Glycol | 0.2 |
| 3-Hydroxypropyl caprylate | Hydroxypropyl caprylate | 0.2 |
| 3-Hydroxypropyl undecylenate | Hydroxypropyl undecylenate | 0.1 |

TABLE 54

Deodorant spray

| Ingredients | Amount |
|---|---|
| PEG-40-hydrogenated castor oil | 3.0 |
| Ethylhexylglycerol (Octoxyglycerol) | 0.2 |
| Ethanol | 40.0 |
| Citrate buffer | 0.5 |
| 1,2-Hexanediol, 1,2-Octanediol (1:1) | 0.3 |
| SymOcide C (o-cymen-5-ol) | 0.05 |
| 2-Benzylheptan-1-ol (Jasmol) | 0.1 |
| Perfume oil PO1, PO2, PO3, PO4, or PO5 | 0.75 |
| Phenoxyethanol | 0.4 |
| 3-Hydroxypropyl caprylate | 0.2 |
| Glyceryl monoundecylenate | 0.1 |
| Water | ad 100 |

TABLE 55

Sunscreen lotion (o/w, broadband protection)

| Ingredients | INCI | Amount |
|---|---|---|
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.1 |
| Glyceryl monoundecylenate | Glyceryl undecylenate | 0.1 |
| Carbopol Ultrez-10 | Carbomer | 0.2 |
| Dow Corning 246 Fluid | Cyclohexasiloxane and Cyclopentasiloxane | 2.0 |
| Dragosantol ® 100* | Bisabolol | 0.3 |
| EDETA BD | Disodium EDTA | 0.1 |
| Emulsiphos ® | Potassium Cetyl Phosphate, Hydrogenated Palm Glycerides | 1.5 |
| Perfume oil PO1, PO2, PO3, PO4, or PO5 | Fragrance | 0.4 |
| Frescolat ®MGA | Menthone Glycerol Acetal | 0.3 |
| Glycerol 85% | Glycerin | 4.7 |
| Keltrol RD | Xanthan Gum | 0.2 |
| Lanette O | Cetearyl Alcohol | 1.0 |
| Neo Heliopan ® 357 | Butyl Methoxy-dibenzoyl-methane | 1.0 |
| Neo Heliopan ® AP (10% as sodium salt) | Disodium Phenyl Dibenzimidazole Tetrasulfonate | 10.0 |
| Neo Heliopan ® AV | Ethylhexyl Methoxy-cinnamate | 3.0 |
| Neo Heliopan ® Hydro (15% as sodium salt) | Phenylbenz-imidazole Sulfonic Acid | 6.7 |
| Neo Heliopan ® MBC | 4-Methylbenzyl-idene Camphor | 1.5 |
| Neo Heliopan ® OS | Ethylhexyl Salicylate | 5.0 |
| Neutral Oil | Caprylic/Capric Triglyceride | 2.0 |
| SymMatrix ® | Maltodextrin, Rubus Fruticosus (Blackberry) Leaf Extract | 0.3 |
| SymOcide ® BHO | Hydroxyacetophenone, Benzyl alcohol, Caprylyl glycol, Aqua | |
| Tegosoft TN | C12-15 Alkyl Benzoate | 5.0 |
| Tocopherol Acetate | Tocopheryl Acetate | 0.5 |
| Triethanolamine, 99% | Triethanolamine | 0.5 |
| Water (demineralized) | Water (Aqua) | ad 100 |

TABLE 56

Emulsion with UV-A/B-broadband protection

| Ingredients | INCI | Amount |
|---|---|---|
| 3-Hydroxypropyl caprylate | Hydroxypropyl caprylate | 0.1 |
| Glyceryl monocaprylate | Glyceryl caprylate | 0.1 |
| 3-Hydroxypropyl undecylenate | Hydroxypropyl undecylenate | 0.05 |
| Glyceryl monoundecylenate | Glyceryl undecylenate | 0.05 |
| Abil 350 | Dimethicone | 0.3 |
| Butylene Glycol | Butylene Glycol | 3.0 |
| Carbopol Ultrez-10 | Carbomer | 0.2 |
| Citric Acid 10% sol. | Citric Acid | 0.3 |
| Dragosantol ® 100* | Bisabolol | 0.1 |
| EDETA BD | Disodium EDTA | 0.1 |
| Emulsiphos ® | Potassium Cetyl Phosphate, Hydrogenated Palm Glycerides | 1.5 |
| Perfume oil PO1, PO2, PO3, PO4, or PO5 | Fragrance | 0.1 |
| Frescolat ®X-COOL | Menthyl Ethylamido Oxalate | 1.0 |
| Glyceryl Stearate | Glyceryl Stearate | 2.0 |
| Keltrol RD | Xanthan Gum | 0.2 |
| Lanette 16 | Cetyl Alcohol | 1.2 |
| Lanette E | Sodium Cetearyl Sulfate | 0.7 |
| Neo Heliopan ® AP (10% as sodium salt) | Disodium Phenyl Dibenzimidazole Tetrasulfonate | 22.0 |
| Neo Heliopan ® HMS | Homosalate | 5.0 |
| Neutral Oil | Caprylic/Capric Triglyceride | 2.0 |
| PCL Liquid 100 | Cetearyl Ethylhexoate | 3.0 |
| Sodium Hydroxide (10% sol.) | Sodium Hydroxide | 2.8 |
| Symdiol ®68 | 1,2-Hexanediol, Caprylylglycol | 0.5 |
| SymMollient ®S | Cetearyl Nonanoate | 1.5 |
| SymSitive ® 1609 | Pentylene Glycol, 4-t-Butylcyclohexanol | 0.5 |
| SymWhite ®377 | Phenylethyl Resorcinol | 0.5 |
| Tocopherol Acetate | Tocopheryl Acetate | 0.5 |
| Water (demineralized) | Water (Aqua) | ad 100 |

TABLE 57

Sun protection soft cream (w/o), SPF 40

| Ingredients | INCI | Amount |
|---|---|---|
| Dehymuls PGPH | Polyglyceryl-2 dipolyhydroxystearate | 5.0 |
| Copherol 1250 | Tocopheryl acetate | 0.5 |
| Permulgin 3220 | Ozocerite | 0.5 |
| Zinc stearate | Zinc stearate | 0.5 |
| Tegosoft TN | C12-15 Alkyl benzoate | 10.0 |
| Neo Heliopan ® E1000 | Isoamyl-p-methoxycinnamate | 2.0 |
| Neo Heliopan ® 303 | Octocrylene | 5.0 |
| Neo Heliopan ® MBC | 4-Methylbenzylidene camphor | 3.0 |
| Zinc oxide, neutral | Zinc oxide | 5.0 |
| Water, distilled | Water (aqua) | ad 100 |
| EDETA BD | Disodium EDTA | 0.1 |
| Glycerol | Glycerol | 4.0 |
| Magnesium sulfate | Magnesium sulfate | 0.5 |
| Perfume oil PO1, PO2, PO3, PO4, or PO5 | Fragrance | 0.3 |
| Symdiol ® 68 | 1,2-Hexanediol, Caprylylglycol | 0.3 |
| 3-Hydroxypropyl caprylate | Hydroxypropyl caprylate | 0.15 |
| Glyceryl monocaprylate | Glyceryl caprylate | 0.15 |

TABLE 58

Sun protection milk (w/o)

| Ingredients | INCI | Amount |
|---|---|---|
| Dehymuls PGPH | Polyglyceryl-2 dipolyhydroxystearate | 3.0 |
| Beeswax 8100 | Beeswax | 1.0 |
| Monomuls 90-0-18 | Glyceryl oleate | 1.0 |
| Zinc stearate | Zinc stearate | 1.0 |
| Cetiol SN | Cetearyl isononanoate | 5.0 |
| Cetiol OE | Dicaprylyl ether | 5.0 |
| Tegosoft TN | C12-15 alkyl benzoate | 4.0 |
| Vitamin E | Tocopherol | 0.5 |
| Neo Heliopan ® OS | Ethylhexyl salicylate | 5.0 |
| Neo Heliopan ® AV | Ethylhexyl methoxycinnamate | 7.5 |
| Uvinul ® T150 | Ethylhexyl triazone | 1.5 |
| Water, distilled | Water (Aqua) | ad 100 |
| Trilon BD | Disodium EDTA | 0.1 |
| Glycerol | Glycerol | 5.0 |
| Neo Heliopan ® AP 10% solution, neutralized with NaOH | Disodium phenyl dibenzimidazole tetrasulfonate | 15.0 |
| Perfume oil PO1, PO2, PO3, PO4, or PO5 | Fragrance | 0.25 |
| Alpha bisabolol | Bisabolol | 0.1 |
| SymOcide ® PT | Phenoxyethanol, Tropolone | 0.25 |
| 3-Hydroxypropyl caprylate | Hydroxypropyl caprylate | 0.2 |
| 3-Hydroxypropyl undecylenate | Hydroxypropyl undecylenate | 0.1 |

TABLE 59

Sun spray with UV-A/B-broadband protection with low oil content

| Ingredients | INCI | Amount |
|---|---|---|
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.05 |
| Glyceryl monoundecylenate | Glyceryl undecylenate | 0.05 |
| Ethanol 96% | Ethanol | 13.0 |
| Perfume oil PO1, PO2, PO3, PO4, or PO5 | Fragrance | 0.5 |
| Glyceryl Stearate | Glyceryl Stearate | 4.0 |
| Hydroviton ® PLUS | Water, Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium hyaluronate, Glucose | 1.0 |
| Isoadipate ® | Diisopropyl Adipate | 1.0 |
| Neo Heliopan ® AV | Ethylhexyl Methoxy-cinnamate | 25.0 |
| Neo Heliopan ® MBC | 4-Methylbenzyl-idene Camphor | 33.3 |
| Propylene Glycol | Propylene Glycol | 0.8 |
| Tego Betain L7 | Cocamidopropyl Betaine | 1.0 |
| Water (demineralized) | Water (Aqua) | ad 100 |

TABLE 60

Sunscreen spray o/w, SPE 15-20

| Ingredients | INCI | Amount |
|---|---|---|
| Dracorin ® GOC | Glyceryl Oleate Citrate, Caprylic/Capric Triglyceride | 2.0 |
| Corapan ® TQ | Diethylhexyl 2,6-Naphthalate | 3.0 |
| Neo Heliopan ® HMS | Homosalate | 7.0 |
| Neo Heliopan ® OS | Ethylhexyl Salicylate | 5.0 |
| Neo Heliopan ® 357 | Butyl Methoxydibenzoylmethane | 3.0 |
| Isoadipate | Diisopropyl Adipate | 6.0 |
| Baysilone ® Oil M10 | Dimethicone | 1.0 |
| Edeta ® BD | Disodium EDTA | 0.1 |
| Vitamin E Acetate | Tocopheryl Acetate | 0.5 |
| Dragosantol ® 100 | Bisabolol | 0.1 |
| Pemulen ® TR-2 | Acrylates/C10-30 Alkyl Acrylate Crosspolymer | 0.25 |
| Water | Water (Aqua) | ad 100 |
| Glycerol 99, 5 P. | Glycerol | 4.0 |
| Butylene Glycol | Butylene Glycol | 5.0 |
| Neo Heliopan ® Hydro (103089), used as 25% aq. solution neutralized with Biotive ® L-Arginine | Phenylbenzimidazole Sulfonic Acid | 8.0 |
| Biotive ® L-Arginine | Arginine | 0.55 |
| Perfume oil PO1, PO2, PO3, PO4, or PO5 | Fragrance | 0.4 |
| SymOcide PS | Phenoxyethanol, 1,2-Hexanediol, Decylene glycol | 0.8 |
| Glyceryl monocaprylate | Glyceryl caprylate | 0.2 |
| 3-Hydroxypropyl undecylenate | Hydroxypropyl undecylenate | 0.1 |

TABLE 61

After sun gel

| Ingredients | INCI | Amount |
|---|---|---|
| SymSol ® PF-3 | Water (Aqua), Pentylene Glycol, Sodium Lauryl Sulfoacetate, Sodium Oleoyl Sarcosinate, Sodium Chloride, Disodium Sulfoacetate, Sodium Oleate, Sodium Sulfate | 3.0 |
| Glycerol 99, 5 P. | Glycerol | 5.0 |
| SymHelios ® 1031 | Benzylidene Dinnethoxydimethylin danone | 0.1 |
| Water | Water (Aqua) | ad 100 |
| Pemulen ® TR-2 | Acrylates/C10-30 Alkyl Acrylate Crosspolymer | 1.0 |
| D-Panthenol 75 W | Panthenol | 0.5 |
| SymFinity ® 1298 | Echinacea Purpurea Extract | 0.1 |
| Extrapone ® Pearl GW | Water (Aqua), Glycerol, Hydrolyzed Pearl, Xanthan Gum | 1.0 |
| Sodium Hydroxide 10% solution | Sodium Hydroxide | 2.5 |
| Ethanol 96% | Alcohol Denat. | 15.0 |
| Perfume oil PO1, PO2, PO3, PO4, or PO5 | Fragrance | 0.2 |

TABLE 61-continued

After sun gel

| Ingredients | INCI | Amount |
|---|---|---|
| SymOcide ® PS | Phenoxyethanol, 1,2-Hexanediol, Decyleneglycol | 0.8 |
| 3-Hydroxypropyl caprylate | Hydroxypropyl caprylate | 0.15 |
| 3-Hydroxypropyl undecylenate | Hydroxypropyl undecylenate | 0.05 |

TABLE 62

After sun lotion

| Ingredients | Amount |
|---|---|
| Acrylate/C10-30 alkylacrylate crosspolymer | 0.4 |
| Cetearylethyl hexanoate | 15.0 |
| Bisabolol | 0.2 |
| Tocopheryl acetate | 1.0 |
| Panthenol | 1.0 |
| Alcohol | 15.0 |
| Glycerol | 3.0 |
| Perfume oil PO1, PO2, PO3, PO4, or PO5 | 0.30 |
| 1,2-Hexanediol | 1.0 |
| 4-Hydroxyacetophenone | 0.3 |
| Pentylene glycol | 4.0 |
| Aqua dem. | ad 100 |
| Triethanolamine | 0.2 |
| 3-Hydroxypropyl caprylate | 0.2 |
| 3-Hydroxypropyl undecylenate | 0.1 |

Example 63 Syndet antimicrobial soap bar

| Ingredients | INCI | Amount |
|---|---|---|
| Zetesap 813 A | Disodium Lauryl Sulfosuccinate, Sodium Lauryl Sulfate, Corn Starch, Cetearyl Alcohol, Paraffin, Titanium Dioxide | ad 100 |
| Amphotensid GB 2009 | Disodium Cocoamphodiacetate | 6.0 |
| Allantoin | Allantoin | 1.0 |
| Perfume oil PO1, PO2, PO3, PO4, or PO5 | Fragrance | 1.0 |
| SymOcide C | o-cymen-5-ol | 0.1 |
| 3-Hydroxypropyl caprylate | Hydroxypropyl caprylate | 0.1 |
| Glyceryl monocaprylate | Glyceryl caprylate | 0.1 |
| 3-Hydroxypropyl undecylenate | Hydroxypropyl undecylenate | 0.05 |
| Glyceryl monoundecylenate | Glyceryl undecylenate | 0.05 |

TABLE 64

Syndet soap bar

| Ingredients | INCI | Amount |
|---|---|---|
| Fenopon AC-78 | Sodium Cocoyl Isethionate | 20.0 |
| Natriumlaurylsulfoacetate | Sodium Lauryl Sulfoacetate | 16.0 |
| Paraffin | Paraffin | 19.0 |
| Wax, microcrystalline | Microcrystalline Wax | 1.0 |
| Corn Starch | Corn Starch | 8.0 |
| Coconut acid | Coconut acid | 2.0 |
| Lauric acid diethanol amide | Lauramide DEA | 2.0 |
| Dextrin | Dextrin | 21.0 |
| Lactic acid, 88% | Lactic Acid | 1.0 |
| SymGuard CD | 3-Phenylpropanol, o-cymen-5-ol, Decylene glycol | 0.3 |
| Thymol | Thymol | 0.05 |
| Water | Water | ad 100 |
| Perfume oil PO1, PO2, PO3, PO4, or PO5 | Fragrance | 1.0 |

TABLE 64-continued

Syndet soap bar

| Ingredients | INCI | Amount |
|---|---|---|
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.05 |
| Glyceryl monoundecylenate | Glyceryl undecylenate | 0.05 |

TABLE 65

Antimicrobial toilet soap bar

| Ingredients | Amount |
|---|---|
| Sodium soap from tallow | 60.0 |
| Sodium soap from palm oil | 27.0 |
| Glycerol | 2.0 |
| Sodium Chloride | 0.5 |
| 1-Hydroxyethane-1,1-diphosphonic acid, tetrasodium salt | 0.3 |
| Alpha-Tocopherol | 0.1 |
| Pigment Yellow 1 | 0.02 |
| Water | ad 100 |
| Perfume oil PO1, PO2, PO3, PO4, or PO5 | 3.0 |
| Farnesol | 0.2 |
| 3-Hydroxypropyl caprylate | 0.1 |
| Glyceryl monocaprylate | 0.1 |
| 3-Hydroxypropyl undecylenate | 0.05 |
| Glyceryl monoundecylenate | 0.05 |

TABLE 66

Shaving foam

| Ingredients | Amount |
|---|---|
| Dem. Water | ad 100 |
| Triethanolamine | 4.0 |
| Edenor L2 SM (Stearinic acid, Palmitinic acid) (Cognis) | 5.3 |
| Laureth-23 | 3.0 |
| Stearylalcohol | 0.5 |
| SymOcide BHO (Hydroxacetophenone, Benzyl alcohol, Caprylyl glycol, Water) | 1.0 |
| 3-Hydroxypropyl caprylate | 0.2 |
| Glyceryl monocaprylate | 0.1 |
| 3-Hydroxypropyl undecylenate | 0.1 |
| Glyceryl monoundecylenate | 0.05 |
| Sodium lauryl sulfate | 3.0 |
| Extrapone Seaweed (water, propylene glycol, potassium iodide, Fucus Vesiculosus Extract) | 1.0 |
| Dragosantol (Bisabolol, Farnesol) | 0.1 |
| Perfume oil PO1, PO2, PO3, PO4, or PO5 | 1.0 |
| propane, butane 4,2 Bar | 4.0 |

TABLE 67

Sprayable disinfecting gel

| Ingredients | INCI | Amount |
|---|---|---|
| Water | Water (Aqua) | ad 100 |
| Stabileze QM | PVM/Ma Decadiene Crosspolymer | 0.25 |
| Sodium Hydroxide 10% solution | Sodium Hydroxide | 0.4 |
| Coffein pure | Caffeine | 0.5 |
| Extrapone ® Horse Chestnut | Propylene Glycol, Water (Aqua), Glucose, Aesculus Hippocastanum (Horse Chestnut) Seed Extract, Lactic Acid | 1.0 |
| Hydrolite ® 5 | Pentylene Glycol | 3.0 |
| 1,3 Butylene Glycol | Butylene Glycol | 5.0 |

TABLE 67-continued

Sprayable disinfecting gel

| Ingredients | INCI | Amount |
|---|---|---|
| Biotive ® Esculin Sesquihydrate | Esculin | 0.3 |
| Ethanol 96% | Alcohol Denat. | 10.0 |
| Solubilizer | PEG-40 Hydrogenated Castor Oil, Trideceth-9, Water (Aqua) | 0.5 |
| Perfume oil PO1, PO2, PO3, PO4, or PO5 | Fragrance | 0.2 |
| Octenidine dihydrochloride | | 0.1 |
| Preservative | Phenoxyethanol | 0.7 |
| 3-Hydroxypropyl caprylate | Hydroxypropyl caprylate | 0.15 |
| Glyceryl monocaprylate | Glyceryl caprylate | 0.15 |
| 3-Hydroxypropyl undecylenate | Hydroxypropyl undecylenate | 0.05 |
| Glyceryl monoundecylenate | Glyceryl undecylenate | 0.05 |

TABLE 68

Solution for wet wipes

| Ingredients | INCI | Amount |
|---|---|---|
| SymSol ® PF-3 | Water (Aqua), Pentylene Glycol, Sodium Lauryl Sulfoacetate, SodiumOleoyl Sarcosinate, Sodium Chloride, Disodium Sulfoacetate, SodiumOleate, Sodium Sulfate | 2.0 |
| Dragosantol ® 100 | Bisabolol | 0.1 |
| Glycerol 99, 5 P. | Glycerol | 5.0 |
| Water | Water (Aqua) | ad 100 |
| Hydrolite ® 5 | Pentylene Glycol | 5.0 |
| D-Panthenol 75 W | Panthenol | 0.8 |
| DragoCalm ® | Water (Aqua), Glycerol, Avena Sativa (Oat) Kernel Extract | 1.0 |
| Witch Hazel-Distillate | Hamamelis Virginiana (Witch Hazel) Water, Water (Aqua), Alcohol | 1.0 |
| Allplant Essence ® Org. Rose Geranium P | Pelargonium Graveolens Flower/Leaf/Stem Water | 1.0 |
| Perfume oil PO1, PO2, PO3, PO4, or PO5 | Fragrance | 0.1 |
| SymOcide BHO | Benzyl alcohol, Hydroxyacetophenone, Caprylyl glycol, Water | 0.8 |
| 3-Hydroxypropyl caprylate | Hydroxypropyl caprylate | 0.2 |
| Glyceryl monocaprylate | Glyceryl caprylate | 0.2 |
| 3-Hydroxypropyl undecylenate | Hydroxypropyl undecylenate | 0.1 |
| Glyceryl monoundecylenate | Glyceryl undecylenate | 0.1 |

6. In Vivo Study

An in vivo study was performed to investigate the potential of 3-hydroxypropyl caprylate for anti-dandruff efficacy on scalp. The efficacy was assessed based on the dandruff score according to Piérard-Franchimont, which evaluates the dandruff intensity on a scale from 0-10 (0=none; 1-2=mild; 3-4=moderate; 5-6=marked; 7-8=severe; 9-10=heavy) for 8 individual sections of the scalp. 22 participants with a visual dandruff score of 32 (sum of score over all 8 sections) were included in the study.

The active ingredient was provided in a leave-on pump spray (formulation of 0.5 wt.-% of 3-hydroxypropyl caprylate in ethanol/water 70/30 vol/vol). After two weeks of wash out with an active free shampoo, the test product was applied once daily to the scalp (30 spray bursts, every evening, leave-on overnight) for four weeks, while washing with the active free shampoo continued as during the first two weeks of wash out.

The dandruff scoring was performed after the two weeks of wash out with active free shampoo by a trained technician on day 1 (before first use of the active-containing leave on-pump spray) and day 29 of the treatment with the leave-on pump spray and is depicted in FIG. 5. As shown in FIG. 5, a significant reduction (p=0.004) of the average dandruff score according to Piérard-Franchimont from marked (4.78) to moderate (4.38) took place.

The invention claimed is:

1. An anti-dandruff shampoo comprising:
   an amount from 0.3 to 5 wt. %, based on a total weight of the anti-dandruff shampoo, of one or more fatty acid esters selected from 3-hydroxypropyl caprylate, 3-hydroxypropyl undecylenate, or a mixture thereof, and
   one or more anionic surfactants selected from sodium laureth sulfate, sodium lauryl sulfate, sodium lauryl sulfoacetate, disodium lauryl sulfosuccinate, sodium olefin C14-C16 sulfonate, sodium oleoyl sarcosinate, disodium sulfoacetate, sodium oleate, sodium sulfate, and sodium cocoyl isethionate,
   provided the anti-dandruff shampoo reduces *Malassezia* and/or treats dandruff.

2. The anti-dandruff shampoo of claim 1, further comprising:
   1,2-pentanediol and 3-hydroxypropyl caprylate,
   1,2-pentanediol and 3-hydroxypropyl undecylenate,
   1,2-hexanediol and 3-hydroxypropyl caprylate,
   1,2-hexanediol and 3-hydroxypropyl undecylenate,
   1,2-octanediol and 3-hydroxypropyl caprylate,
   1,2-octanediol and 3-hydroxypropyl undecylenate,
   1,2-decanediol and 3-hydroxypropyl caprylate, or
   1,2-decanediol and 3-hydroxypropyl undecylenate.

3. The anti-dandruff shampoo of claim 1 comprising both the 3-hydroxypropyl caprylate and the 3-hydroxypropyl undecylenate.

4. The anti-dandruff shampoo of claim 1, wherein the dandruff is caused by an excess of the *Malassezia* on the skin.

5. The anti-dandruff shampoo of claim 1, further comprising one or more 1,2-alkane diol(s).

6. The anti-dandruff shampoo of claim 5, wherein the one or more 1,2-alkane diol(s) are selected from 1,2-pentanediol, 1,2-hexanediol, 1,2-octanediol, 1,2-decanediol, or mixtures thereof.

7. The anti-dandruff shampoo of claim 1, wherein the *Malassezia* is *M. furfur, M. pachydermatis, M. sympodialis, M. globosa, M. obtusa, M. restricta, M. slooffiae, M. dermatis, M. japonica, M. nana, M. yamatoensis, M. caprae, M. equina, M. cuniculi, M. brasiliensis, M. psitaci, M. arunalokei*, or mixtures thereof.

8. A method for treating dandruff comprising application of the anti-dandruff shampoo of claim 1 to the skin.

9. The method of claim 8, wherein the anti-dandruff shampoo comprises both the 3-hydroxypropyl caprylate and the 3-hydroxypropyl undecylenate.

10. The method of claim 8, wherein the anti-dandruff shampoo further comprises one or more 1,2-alkane diols selected from 1,2-pentanediol, 1,2-hexanediol, 1,2-octanediol, 1,2-decanediol, or a mixtures thereof.

11. The anti-dandruff shampoo of claim 1 comprising the 3-hydroxypropyl caprylate.

12. The anti-dandruff shampoo of claim 1 comprising the 3-hydroxypropyl undecylenate.

13. The anti-dandruff shampoo of claim 1, wherein application of the anti-dandruff shampoo to skin suffering from dandruff visually reduces the dandruff by more than 10%.

14. The anti-dandruff shampoo of claim 1, wherein application of the anti-dandruff shampoo to skin suffering from excess *Malassezia* reduces the *Malassezia* by more than 10%.

15. A skin or hair care product comprising:
an amount from 0.3 to 5 wt. %, based on a total weight of the skin or hair care product, of one or more fatty acid esters selected from 3-hydroxypropyl caprylate, 3-hydroxypropyl undecylenate, or a mixture thereof,
one or more anionic surfactants selected from sodium laureth sulfate, sodium lauryl sulfate, sodium lauryl sulfoacetate, disodium lauryl sulfosuccinate, sodium olefin C14-C16 sulfonate, sodium oleoyl sarcosinate, disodium sulfoacetate, sodium oleate, sodium sulfate, and sodium cocoyl isethionate,
provided the skin or hair care product is an oil-in-water emulsion or a water-in-oil emulsion, and reduces *Malassezia* and/or treats dandruff.

16. The skin or hair care product of claim 15, wherein application of the skin or hair care product to skin suffering from dandruff visually reduces the dandruff by more than 10%.

17. The skin or hair care product of claim 15, wherein application of the skin or hair care product to skin suffering from excess *Malassezia* reduces the *Malassezia* by more than 10%.

18. The product of claim 15 comprising the 3-hydroxypropyl caprylate.

19. The product of claim 15 comprising the 3-hydroxypropyl undecylenate.

20. A method for treating dandruff comprising application of the skin or hair care product of claim 15 to the skin.

* * * * *